US009920117B2

(12) United States Patent
Ono et al.

(10) Patent No.: US 9,920,117 B2
(45) Date of Patent: Mar. 20, 2018

(54) FUNCTIONAL MONOCLONAL ANTIBODY AGAINST HEPARIN-BINDING EPIDERMAL GROWTH FACTOR-LIKE GROWTH FACTOR

(71) Applicant: MEDICAL & BIOLOGICAL LABORATORIES CO., LTD., Nagoya-shi, Aichi (JP)

(72) Inventors: Kenichiro Ono, Nagoya (JP); Junichi Akatsuka, Ina (JP)

(73) Assignee: MEDICAL & BIOLOGICAL LABORATIVES CO., LTD., Nagoya-shi, Aichi (JP)

( * ) Notice: Subject to any disclaimer, the term of this patent is extended or adjusted under 35 U.S.C. 154(b) by 0 days.

(21) Appl. No.: 14/786,436

(22) PCT Filed: Apr. 17, 2014

(86) PCT No.: PCT/JP2014/060920
§ 371 (c)(1),
(2) Date: Oct. 22, 2015

(87) PCT Pub. No.: WO2014/175160
PCT Pub. Date: Oct. 30, 2014

(65) Prior Publication Data
US 2016/0083464 A1 Mar. 24, 2016

(30) Foreign Application Priority Data

Apr. 23, 2013 (WO) .................. PCT/JP2013/061943

(51) Int. Cl.
*C07K 16/22* (2006.01)
(52) U.S. Cl.
CPC .......... *C07K 16/22* (2013.01); *C07K 2317/24* (2013.01); *C07K 2317/34* (2013.01); *C07K 2317/732* (2013.01); *C07K 2317/76* (2013.01)

(58) Field of Classification Search
None
See application file for complete search history.

(56) References Cited

U.S. PATENT DOCUMENTS

2011/0034673 A1  2/2011  Mekada et al.
2011/0110956 A1  5/2011  Rothe et al.

FOREIGN PATENT DOCUMENTS

JP   2011-501655 A   1/2011
WO  2009/072628 A1  6/2009

OTHER PUBLICATIONS

Cha et al., Infection and Immunity, 70(5):2344-2350, May 2002.*
International Preliminary Report on Patentability dated Oct. 27, 2015, with Written Opinion.
Communication, dated Dec. 12, 2016, issued by the European Patent Office in counterpart European Patent Application No. 14787867.2.
Gerhard Raab et al., "Heparin-binding EGF-like growth factor," Biochimica et Biophysica Acta, 1997, pp. F179-F199, vol. 1333, No. 3.
Minoru Ono et al., "Purification and Characterization of Transmembrane Forms of Heparin-binding EGF-like Growth Factor," The Journal of Biological Chemistry, Dec. 9, 1994, pp. 31315-31321, vol. 269, No. 49.
Klaus Elenius et al., "Activation of HER4 by heparin-binding EGF-like growth factor stimulates chemotaxis but not proliferation," The EMBO Journal, 1997, pp. 1268-1278, vol. 16, No. 6.
Xiaorong Chen et al., "Induction of Heparin-binding EGF-like Growth Factor Expression during Myogenesis," The Journal of Biological Chemistry, Aug. 4, 1995, pp. 18285-18294, vol. 270, No. 31.
Ryo Iwamoto et al., "Heparin-binding EGF-like growth factor and ErbB signaling is essential for heart function," PNAS, Mar. 18, 2003, pp. 3221-3226, vol. 100, No. 6.
Moshe Marikovsky et al., "Appearance of heparin-binding EGF-like growth factor in wound fluid as a response to injury," Proc. Natl. Acad. Sci., May 1993, pp. 3889-3893, vol. 90, No. 9.
Michael S. Kobrin et al., "Induction and Expression of Heparin-Binding EGF-Like Growth Factor in Human Pancreatic Cancer," Biochemical and Biophysical Research Communications, Aug. 15, 1994, pp. 1705-1709, vol. 202, No. 3.
Markus Naef et al., "Co-Expression of Heparin-Binding EGF-Like Growth Factor and Related Peptides in Human Gastric Carcinoma," Int. J. Cancer, Jan. 17, 1996, pp. 315-321, vol. 66, No. 3.
Marc T. Downing et al., "Immunohistochemical localization of heparin-binding epidermal growth factor-like growth factor in normal skin and skin cancers," Histochemical Journal, 1997, pp. 735-744, vol. 29, No. 10.
Hiromitsu Hatakeyama et al., "Regulation of Heparin-Binding EGF-Like Growth Factor by miR-212 and Acquired Cetuximab-Resistance in Head and Neck Squamous Cell Carcinoma," PLoS One, Sep. 2010, pp. 1-13, vol. 5, No. 9.
Pat P. Ongusaha et al., "HB-EGF Is a Potent Inducer of Tumor Growth and Angiogenesis," Cancer Research, Aug. 1, 2004, pp. 5283-5290, vol. 64.
Umut Sahin et al., "Distinct roles for ADAM10 and ADAM17 in ectodomain shedding of six EGFR ligands," The Journal of Cell Biology, Mar. 1, 2004, pp. 769-779, vol. 164, No. 5.

(Continued)

*Primary Examiner* — Marianne P Allen
(74) *Attorney, Agent, or Firm* — Sughrue Mion, PLLC

(57) ABSTRACT

Two types of antibodies (35-1 antibody and 292 antibody) capable of binding to phenylalanine at position 115, isoleucine at position 117, glycine at position 140, glutamic acid at position 141, and arginine at position 142 of a human HB-EGF protein were successfully obtained. Then, it was also found that these antibodies had an activity of suppressing cleavage of the human HB-EGF protein, and an activity of suppressing EGFR phosphorylation that would occur when the human HB-EGF bound to the EGFR. Further, determined were amino acid sequences of light chain and heavy chain variable regions of these antibodies and sequences of CDRs of each of the variable regions.

4 Claims, 11 Drawing Sheets

(56) References Cited

OTHER PUBLICATIONS

Shigeki Higashiyama et al., "Structure of Heparin-binding EGF-like Growth Factor," The Journal of Biological Chemistry, Mar. 25, 1992, pp. 6205-6212, vol. 267, No. 9.
Tsukasa Takemura et al., "The Membrane-bound Form of Heparin-binding Epidermal Growth Factor-like Growth Factor Promotes Survival of Cultured Renal Epithelial Cells," The Journal of Biological Chemistry, Dec. 5, 1997, pp. 31036-31042, vol. 272, No. 49.
Satoru Yamazaki et al., "Mice with defects in HB-EGF ectodomain shedding show severe developmental abnormalities," The Journal of Cell Biology, Nov. 3, 2003, pp. 469-475, vol. 163, No. 3.
Masanori Asakura et al., "Cardiac hypertrophy is inhibited by antagonism of ADAM12 processing of HB-EGF: Metalloproteinase inhibitors as a new therapy," Nature Medicine, Jan. 2002, pp. 35-40, vol. 8, No. 1.
Takaya Shimura et al., "Suppression of proHB-EGF Carboxy-Terminal Fragment Nuclear Translocation: A New Molecular Target Therapy for Gastric Cancer," Clin Cancer Res, Jun. 15, 2008, pp. 3956-3965, vol. 14, No. 12.
Takaya Shimura et al., "Nuclear translocation of the cytoplasmic domain of HB-EGF induces gastric cancer invasion," BMC Cancer, 2012, pp. 1-10, vol. 12, No. 205.
Shingo Miyamoto et al., "Heparin-Binding EGF-Like Growth Factor Is a Promising Target for Ovarian Cancer Therapy," Cancer Research, Aug. 15, 2004, pp. 5720-5727, vol. 64.
Shingo Miyamoto et al., "A Novel Anti-Human HB-EGF Monoclonal Antibody with Multiple Antitumor Mechanisms against Ovarian Cancer Cells," Clinical Cancer Research, 2011, pp. 6733-6741, vol. 17, No. 21.
Miki Hamaoka et al., "Anti-human HB-EGF monoclonal antibodies inhibiting ectodomain shedding of HB-EGF and diphtheria toxin binding," The Journal of Biochemistry, 2010, pp. 55-69, vol. 148, No. 1.
Shuji Sato et al., "A Potent Anti-HB-EGF Monoclonal Antibody Inhibits Cancer Cell Proliferation and Multiple Angiogenic Activities of HB-EGF," PLoS One, Dec. 2012, pp. 1-10, vol. 7, No. 12.
Isamu Tsuji et al., "Characterization of a variety of neutralizing anti-heparin-binding epidermal growth factor-like growth factor monoclonal antibodies by different immunization methods," mAbs, Nov./Dec. 2012, pp. 732-739, vol. 4, No. 6.
International Search Report of PCT/JP2014/060920 filed Jul. 22, 2014.

* cited by examiner

SEQUENCE LISTING

```
<160> NUMBER OF SEQ ID NOS: 22

<210> SEQ ID NO 1
<211> LENGTH: 208
<212> TYPE: PRT
```

<213> ORGANISM: Homo sapiens

<400> SEQUENCE: 1

```
Met Lys Leu Leu Pro Ser Val Val Leu Lys Leu Phe Leu Ala Ala Val
1               5                   10                  15

Leu Ser Ala Leu Val Thr Gly Glu Ser Leu Glu Arg Leu Arg Arg Gly
            20                  25                  30

Leu Ala Ala Gly Thr Ser Asn Pro Asp Pro Pro Thr Val Ser Thr Asp
        35                  40                  45

Gln Leu Leu Pro Leu Gly Gly Gly Arg Asp Arg Lys Val Arg Asp Leu
    50                  55                  60

Gln Glu Ala Asp Leu Asp Leu Leu Arg Val Thr Leu Ser Ser Lys Pro
65                  70                  75                  80

Gln Ala Leu Ala Thr Pro Asn Lys Glu Glu His Gly Lys Arg Lys Lys
                85                  90                  95

Lys Gly Lys Gly Leu Gly Lys Lys Arg Asp Pro Cys Leu Arg Lys Tyr
            100                 105                 110

Lys Asp Phe Cys Ile His Gly Glu Cys Lys Tyr Val Lys Glu Leu Arg
        115                 120                 125

Ala Pro Ser Cys Ile Cys His Pro Gly Tyr His Gly Glu Arg Cys His
    130                 135                 140

Gly Leu Ser Leu Pro Val Glu Asn Arg Leu Tyr Thr Tyr Asp His Thr
145                 150                 155                 160

Thr Ile Leu Ala Val Val Ala Val Val Leu Ser Ser Val Cys Leu Leu
                165                 170                 175

Val Ile Val Gly Leu Leu Met Phe Arg Tyr His Arg Arg Gly Gly Tyr
            180                 185                 190

Asp Val Glu Asn Glu Glu Lys Val Lys Leu Gly Met Thr Asn Ser His
        195                 200                 205
```

<210> SEQ ID NO 2
<211> LENGTH: 10
<212> TYPE: PRT
<213> ORGANISM: Mus musculus
<220> FEATURE:
<221> NAME/KEY: SITE
<222> LOCATION: (1)..(10)
<223> OTHER INFORMATION: CDR1 of Light Chain(35-1)

<400> SEQUENCE: 2

```
Ser Ala Ser Ser Ser Val Thr Tyr Met Tyr
1               5                   10
```

<210> SEQ ID NO 3
<211> LENGTH: 7
<212> TYPE: PRT
<213> ORGANISM: Mus musculus
<220> FEATURE:
<221> NAME/KEY: SITE
<222> LOCATION: (1)..(7)
<223> OTHER INFORMATION: CDR2 of Light Chain(35-1)

<400> SEQUENCE: 3

```
Asp Thr Ser Asn Leu Ala Ser
1               5
```

<210> SEQ ID NO 4
<211> LENGTH: 9
<212> TYPE: PRT
<213> ORGANISM: Mus musculus
<220> FEATURE:

```
<221> NAME/KEY: SITE
<222> LOCATION: (1)..(9)
<223> OTHER INFORMATION: CDR3 of Light Chain(35-1)

<400> SEQUENCE: 4

Gln Gln Trp Ser Ser Tyr Pro Pro Thr
1               5

<210> SEQ ID NO 5
<211> LENGTH: 106
<212> TYPE: PRT
<213> ORGANISM: Mus musculus
<220> FEATURE:
<221> NAME/KEY: SITE
<222> LOCATION: (1)..(106)
<223> OTHER INFORMATION: Variable Region of Light Chain(35-1)

<400> SEQUENCE: 5

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Thr Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Pro Thr
                85                  90                  95

Phe Gly Gly Gly Thr Lys Leu Glu Ile Lys
            100                 105

<210> SEQ ID NO 6
<211> LENGTH: 5
<212> TYPE: PRT
<213> ORGANISM: Mus musculus
<220> FEATURE:
<221> NAME/KEY: SITE
<222> LOCATION: (1)..(5)
<223> OTHER INFORMATION: CDR1 of Heavy Chain(35-1)

<400> SEQUENCE: 6

Gly Tyr Tyr Met His
1               5

<210> SEQ ID NO 7
<211> LENGTH: 17
<212> TYPE: PRT
<213> ORGANISM: Mus musculus
<220> FEATURE:
<221> NAME/KEY: SITE
<222> LOCATION: (1)..(17)
<223> OTHER INFORMATION: CDR2 of Heavy Chain(35-1)

<400> SEQUENCE: 7

Glu Ile Asn Pro Ser Thr Gly Gly Ile Thr Tyr Asn Gln Lys Phe Lys
1               5                   10                  15

Ala

<210> SEQ ID NO 8
<211> LENGTH: 7
<212> TYPE: PRT
<213> ORGANISM: Mus musculus
```

```
<220> FEATURE:
<221> NAME/KEY: SITE
<222> LOCATION: (1)..(7)
<223> OTHER INFORMATION: CDR3 of Heavy Chain(35-1)

<400> SEQUENCE: 8

Ile Thr Trp Ala Phe Ala Tyr
1               5

<210> SEQ ID NO 9
<211> LENGTH: 116
<212> TYPE: PRT
<213> ORGANISM: Mus musculus
<220> FEATURE:
<221> NAME/KEY: SITE
<222> LOCATION: (1)..(116)
<223> OTHER INFORMATION: Variable Region of Heavy Chain(35-1)

<400> SEQUENCE: 9

Glu Val Gln Leu Gln Gln Ser Gly Pro Glu Leu Val Lys Pro Arg Ala
1               5                   10                  15

Ser Val Lys Ile Ser Cys Lys Ala Ser Gly Tyr Ser Phe Ser Gly Tyr
            20                  25                  30

Tyr Met His Trp Val Lys Gln Ser Pro Glu Lys Ser Leu Glu Trp Ile
        35                  40                  45

Gly Glu Ile Asn Pro Ser Thr Gly Gly Ile Thr Tyr Asn Gln Lys Phe
    50                  55                  60

Lys Ala Lys Ala Thr Leu Thr Val Asp Arg Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Thr Arg Ile Thr Trp Ala Phe Ala Tyr Trp Gly Gln Gly Thr Leu Val
            100                 105                 110

Thr Val Ser Ala
        115

<210> SEQ ID NO 10
<211> LENGTH: 10
<212> TYPE: PRT
<213> ORGANISM: Mus musculus
<220> FEATURE:
<221> NAME/KEY: SITE
<222> LOCATION: (1)..(10)
<223> OTHER INFORMATION: CDR1 of Light Chain(292)

<400> SEQUENCE: 10

Ser Ala Ser Ser Ser Ile Ser Tyr Met Tyr
1               5                   10

<210> SEQ ID NO 11
<211> LENGTH: 7
<212> TYPE: PRT
<213> ORGANISM: Mus musculus
<220> FEATURE:
<221> NAME/KEY: SITE
<222> LOCATION: (1)..(7)
<223> OTHER INFORMATION: CDR2 of Light Chain(292)

<400> SEQUENCE: 11

Asp Thr Ser Asn Leu Ala Ser
1               5

<210> SEQ ID NO 12
<211> LENGTH: 9
```

```
<212> TYPE: PRT
<213> ORGANISM: Mus musculus
<220> FEATURE:
<221> NAME/KEY: SITE
<222> LOCATION: (1)..(9)
<223> OTHER INFORMATION: CDR3 of Light Chain(292)

<400> SEQUENCE: 12

Gln Gln Trp Ser Ser Tyr Pro Ser Thr
1               5

<210> SEQ ID NO 13
<211> LENGTH: 106
<212> TYPE: PRT
<213> ORGANISM: Mus musculus
<220> FEATURE:
<221> NAME/KEY: SITE
<222> LOCATION: (1)..(106)
<223> OTHER INFORMATION: Variable Region of Light Chain(292)

<400> SEQUENCE: 13

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Ile Ser Tyr Met
            20                  25                  30

Tyr Trp Tyr Gln Gln Arg Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser His Ser Leu Thr Ile Ser Arg Met Glu Ala Glu
65                  70                  75                  80

Asp Ala Ala Thr Tyr Tyr Cys Gln Gln Trp Ser Ser Tyr Pro Ser Thr
                85                  90                  95

Phe Gly Gly Gly Thr Lys Leu Glu Ile Lys
            100                 105

<210> SEQ ID NO 14
<211> LENGTH: 5
<212> TYPE: PRT
<213> ORGANISM: Mus musculus
<220> FEATURE:
<221> NAME/KEY: SITE
<222> LOCATION: (1)..(5)
<223> OTHER INFORMATION: CDR1 of Heavy Chain(292)

<400> SEQUENCE: 14

Gly Tyr Tyr Met His
1               5

<210> SEQ ID NO 15
<211> LENGTH: 17
<212> TYPE: PRT
<213> ORGANISM: Mus musculus
<220> FEATURE:
<221> NAME/KEY: SITE
<222> LOCATION: (1)..(17)
<223> OTHER INFORMATION: CDR2 of Heavy Chain(292)

<400> SEQUENCE: 15

Glu Ile Asn Pro Ser Thr Gly Gly Thr Thr Tyr Asn Gln Lys Phe Lys
1               5                   10                  15

Ala

<210> SEQ ID NO 16
```

```
<211> LENGTH: 8
<212> TYPE: PRT
<213> ORGANISM: Mus musculus
<220> FEATURE:
<221> NAME/KEY: SITE
<222> LOCATION: (1)..(8)
<223> OTHER INFORMATION: CDR3 of Heavy Chain(292)

<400> SEQUENCE: 16

Ser Pro Tyr Trp Asp Gly Ala Tyr
1               5

<210> SEQ ID NO 17
<211> LENGTH: 117
<212> TYPE: PRT
<213> ORGANISM: Mus musculus
<220> FEATURE:
<221> NAME/KEY: SITE
<222> LOCATION: (1)..(117)
<223> OTHER INFORMATION: Variable Region of Heavy Chain(292)

<400> SEQUENCE: 17

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser Pro Glu Lys Ser Leu Glu Trp Ile
        35                  40                  45

Gly Glu Ile Asn Pro Ser Thr Gly Gly Thr Thr Tyr Asn Gln Lys Phe
    50                  55                  60

Lys Ala Lys Ala Thr Leu Thr Leu Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Lys Ser Pro Tyr Trp Asp Gly Ala Tyr Trp Gly Gln Gly Thr Leu
            100                 105                 110

Val Thr Val Ser Ala
        115

<210> SEQ ID NO 18
<211> LENGTH: 106
<212> TYPE: PRT
<213> ORGANISM: Artificial Sequence
<220> FEATURE:
<223> OTHER INFORMATION: Synthetic Humanized Variable Region of Light
      Chain (35-1)

<400> SEQUENCE: 18

Gln Ile Val Leu Thr Gln Ser Pro Thr Thr Met Ala Ala Ser Pro Gly
1               5                   10                  15

Glu Lys Ile Thr Ile Thr Cys Ser Ala Ser Ser Ser Val Thr Tyr Met
            20                  25                  30

Tyr Trp Tyr Gln Gln Arg Pro Gly Phe Ser Pro Lys Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Gly Thr Met Glu Ala Glu
65                  70                  75                  80

Asp Val Ala Thr Tyr Tyr Cys Gln Gln Trp Ser Ser Tyr Pro Pro Thr
                85                  90                  95

Phe Gly Gly Gly Thr Lys Leu Glu Ile Lys
```

```
<210> SEQ ID NO 19
<211> LENGTH: 116
<212> TYPE: PRT
<213> ORGANISM: Artificial Sequence
<220> FEATURE:
<223> OTHER INFORMATION: Synthetic Humanized Variable Region of Heavy
      Chain (35-1)

<400> SEQUENCE: 19

Gln Val Gln Leu Val Gln Ser Gly Ala Glu Val Val Lys Pro Gly Ser
1               5                   10                  15

Ser Val Lys Val Ser Cys Lys Ala Ser Gly Tyr Ser Phe Ser Gly Tyr
            20                  25                  30

Tyr Met His Trp Val Lys Gln Ala Pro Gly Gln Gly Leu Glu Trp Ile
        35                  40                  45

Gly Glu Ile Asn Pro Ser Thr Gly Gly Ile Thr Tyr Asn Gln Lys Phe
    50                  55                  60

Lys Ala Lys Ala Thr Leu Thr Val Asp Arg Ser Thr Ser Thr Ala Tyr
65                  70                  75                  80

Met Glu Leu Lys Ser Leu Thr Ser Glu Asp Thr Ala Val Tyr Tyr Cys
                85                  90                  95

Thr Arg Ile Thr Trp Ala Phe Ala Tyr Trp Gly Gln Gly Thr Thr Val
            100                 105                 110

Thr Val Ser Ser
        115

<210> SEQ ID NO 20
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 20
cgactggagc acgaggacac tga                                        23

<210> SEQ ID NO 21
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 21
aattttcttg tccacctgg                                             19

<210> SEQ ID NO 22
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 22
ctaacactca ttcctgttga agctct                                     26
```

FUNCTIONAL MONOCLONAL ANTIBODY AGAINST HEPARIN-BINDING EPIDERMAL GROWTH FACTOR-LIKE GROWTH FACTOR

CROSS REFERENCE TO RELATED APPLICATIONS

This is a National Stage of International Application No. PCT/JP2014/060920 filed Apr. 17, 2014, claiming priority based on International Patent Application No. PCT/JP2013/061943 filed Apr. 23, 2013, the contents of all of which are incorporated herein by reference in their entirety.

TECHNICAL FIELD

The present invention relates to an antibody against a human HB-EGF protein, a DNA encoding the antibody, a hybridoma comprising any one of the antibody and the DNA, and a composition for treating or preventing a cancer, the composition comprising the antibody as an active ingredient.

BACKGROUND ART

A heparin-binding epidermal growth factor-like growth factor (HB-EGF) is a protein belonging to the epidermal growth factor (EGF) family. It has been revealed that this protein promotes cell proliferation, differentiation, chemotaxis, and so forth by binding to an EGF receptor (EGFR/ErbB1 or ErbB4) (NPLs 1 to 3).

Moreover, it has been revealed that HB-EGF in vivo contributes to myogenesis, heart development, and wound healing. This suggests that HB-EGF is an important factor in organogenesis (NPLs 4 to 6).

Further, there have been reports that HB-EGF is involved in cancer proliferation and progression at a variety of aspects such as the proliferation of pancreatic cancer (NPL 7), the proliferation of stomach cancer (NPL 8), the association with skin cancer (NPL 9), the association with drug resistance in head and neck cancers (NPL 10), and angiogenesis to cancer tissues (NPL 11). It has been revealed that HB-EGF is an important factor also in various cancers.

Moreover, it has been revealed that HB-EGF is first synthesized in the form of a type I transmembrane protein (transmembrane HB-EGF), and then an extracellular region immediately above a cell transmembrane portion in the cell membrane is cleaved by a protease and subsequently released in the form of 14- to 22-kilodalton soluble HB-EGF (NPLs 12 and 13). Further, it is also known that soluble HB-EGF formed by such cleavage functions as a growth factor which activates EGFR/ErbB1 of its own HB-EGF expressing cell in an autocrine manner, or which activates EGFR/ErbB1 of the other cells in a paracrine manner.

On the other hand, it is known that transmembrane HB-EGF itself also functions as a growth factor which activates EGFR/ErbB1 of other nearby cells in a juxtacrine manner (NPL 14). However, it has been shown that the cell proliferating activity of transmembrane HB-EGF is weaker than that of soluble HB-EGF (NPL 11). These results suggest the process of forming soluble HB-EGF by protease cleavage is important in making HB-EGF exhibit the function as a growth factor.

Meanwhile, mutant mice prepared to express transmembrane HB-EGF but not to express soluble HB-EGF have been produced by introducing an amino acid mutation into a cleavage site of HB-EGF. Then, in the analysis of the mutant mice, abnormal heart organogenesis has been observed as in the case of knockout mice which express no HB-EGF at all (NPLs 5 and 15). Further, it has also been shown that suppressing the HB-EGF cleavage by a protease inhibitor suppresses cardiac hypertrophy due to soluble HB-EGF (NPL 16). This suggests that soluble HB-EGF plays a role in the aforementioned important physiological function of HB-EGF in the organogenesis.

Moreover, it is also known that, in a cancer, a cleaved intracellular region (HB-EGF-CTF) of HB-EGF is translocated to the nucleus and functions to promote the cell division (NPL 17). Further, it has been shown that suppressing the HB-EGF cleavage by a protease inhibitor can inhibit the proliferation and invasion of stomach cancer (NPL 18). Hence, it has been revealed that the HB-EGF cleaving process is an important factor in the proliferation and so forth of cancer cells, too.

Based on the above-described findings, researches and developments have been in progress for treatment methods against various diseases (such as heart failure, nerve diseases, lung diseases), particularly cancers, in which HB-EGF is presumably involved. For example, the anti-tumor effect of an anti-HB-EGF antibody or the like has been confirmed in a xenograft mouse model obtained by transplanting ovarian cancer cells (NPLs 19 and 20). Further, it has also been shown that the proliferation of cancer cells can be inhibited by inhibiting the HB-EGF cleavage using an antibody to suppress soluble HB-EGF formation (NPL 21). As such, antibodies have been developed which are capable of binding to HB-EGF and exhibiting such activities as anti-tumor activity and cleavage inhibitory activity.

As described above, in order for an antibody against HB-EGF to have sufficient activities in the treatments against cancers or the like, in other words, to completely block signal transduction in cell proliferation or the like in which HB-EGF is involved, it is presumably necessary that such an antibody should have both of two activities: (1) strongly inhibiting the cleavage that would lead to the formation of soluble HB-EGF and HB-EGF-CTF functioning as a growth factor or the like (cleavage inhibitory activity); and (2) inhibit binding of soluble HB-EGF and transmembrane HB-EGF to an EGF receptor (EGFR/ErbB1 or ErbB4), consequently strongly inhibiting the activation and so forth of the EGF receptor (neutralizing activity).

Nevertheless, for example, the antibody described in NPL 21 has a cleavage inhibitory activity as described above, but this literature has also revealed that the antibody does not have a neutralizing activity. Judging from the foregoing, under current situations, no antibody against HB-EGF has been developed which has sufficient activities in the treatments of diseases, particularly cancers, in which HB-EGF is involved.

CITATION LIST

Non Patent Literatures

[NPL 1] Raab G., Biochim Biophys Acta, 1997, vol. 1333, iss. 3, F179 to F199
[NPL 2] Ono M. et al., J. Biol. Chem., 1994, vol. 269 no. 49, pp. 31315 to 31321
[NPL 3] Elenius K. et al., EMBO J., 1997, vol. 16, iss. 6, pp. 1268 to 1278
[NPL 4] Chen, X. et al., J. Biol. Chem., 1995, vol. 270, pp. 18285 to 18294
[NPL 5] Iwamoto R. et al., PNAS, 2003, vol. 100, no. 6, pp. 3221 to 3226

[NPL 6] Marikovsky M. et al., PNAS, 1993, vol. 90, no. 9, pp. 3889 to 3893
[NPL 7] Kobrin M. S. et al., BBRC, 1994, vol. 202, iss. 3, pp. 1705 to 1709
[NPL 8] Naef M. et al., Int J Cancer, 1996, vol. 66, iss. 3, pp. 315 to 321
[NPL 9] Downing M. T. et al., Histochem J., 1997, vol. 29, iss. 10, pp. 735 to 744
[NPL 10] Hatakeyama H. et al., PLosOne, 2010, vol. 5, iss. 9, e12702
[NPL 11] Ongusaha P. et al., Cancer res., 2004, vol. 64, pp. 5283 to 5290
[NPL 12] Sahin U. et al., J Cell Biol., 2004, vol. 164, no. 5, pp. 769 to 779
[NPL 13] Higashiyama S. et al., J. Biol. Chem., 1992, vol. 267, no. 9, pp. 6205 to 6212
[NPL 14] Takemura T. et al., J. Biol. Chem., 1997, vol. 272, pp. 31036 to 31042
[NPL 15] Yamazaki S. et al., J Cell Biol., 2003, vol. 163, no. 3, pp. 469 to 475
[NPL 16] Asakura M. et al., Nat Med., 2002, vol. 8, no. 1, pp. 35 to 40
[NPL 17] Shimura T. et al., Clin Cancer Res., 2008, vol. 14, no. 12, pp. 3956 to 3965
[NPL 18] Shimura T. et al., BMC Cancer, 2012, 12: 205
[NPL 19] Miyamoto S. et al., Cancer Res., 2004, vol. 64, pp. 5720 to 5727
[NPL 20] Miyamoto S. et al., Clin Cancer Res., 2011, vol. 17, no. 21, pp. 6733 to 6741
[NPL 21] Hamaoka M. et al., J. Biochem., 2010, vol. 148, no. 1, pp. 55 to 69

SUMMARY OF INVENTION

Technical Problem

The present invention has been made in view of the above-described problem of the conventional techniques. An object of the present invention is to provide an antibody capable of binding to human HB-EGF, thereby inhibiting cleavage of the human HB-EGF and inhibiting binding between the human HB-EGF and an EGF receptor.

Solution to Problem

In order to achieve the object, the present inventors immunized mice with a partial peptide containing an extracellular region of an HB-EGF protein, and obtained monoclonal antibodies against a human HB-EGF protein. Then, among the obtained anti-human HB-EGF monoclonal antibodies, three antibodies (35-1 antibody, 292 antibody, and 1-1 antibody) were selected which exhibited a strong reactivity with HB-EGF expressed on the cell surface.

Further, the result of analyzing epitopes for these antibodies revealed that the 35-1 antibody and the 292 antibody recognized phenylalanine at position 115, isoleucine at position 117, glycine at position 140, glutamic acid at position 141, and arginine at position 142 of the human HB-EGF protein. On the other hand, it was revealed that the 1-1 antibody recognized phenylalanine at position 115, glycine at position 140, glutamic acid at position 141, and arginine at position 142, but did not recognize isoleucine at position 117 unlike the two antibodies.

Moreover, the antibodies were earnestly studied. As a result, it was found that any of the 35-1 antibody and the 292 antibody was able to inhibit the cleavage of the human HB-EGF. Further, it was also found that any of the antibodies was able to suppress phosphorylation of an EGF receptor (EGFR) that would occur when human HB-EGF bound to the EGFR, in other words, the antibodies had a neutralizing activity. On the other hand, the 1-1 antibody had a cleavage inhibitory activity, but did not have a neutralizing activity. This revealed that since recognizing isoleucine at position 117 of the human HB-EGF protein also, the 35-1 antibody and the 292 antibody had a cleavage inhibitory activity and a neutralizing activity; meanwhile, since not recognizing isoleucine at position 117, the 1-1 antibody did not have a neutralizing activity. It was revealed that, in order for an anti-HB-EGF antibody to exhibit a strong neutralizing activity, it was necessary for the anti-HB-EGF antibody to bind to isoleucine at position 117 of the human HB-EGF protein.

Furthermore, the present inventors determined sequences of heavy chain and light chain variable regions and CDRs of the 35-1 antibody and the 292 antibody having such cleavage inhibitory activity and neutralizing activity. Further, based on the determined sequences, a chimeric antibody of the 35-1 antibody was prepared which had the constant region substituted with one derived from human IgG; in addition, a humanized antibody of the 35-1 antibody was prepared which had framework regions of the variable regions substituted with ones from a human antibody. Then, it was also revealed that administering the obtained chimeric antibody to mice into which cancer cells had been transplanted suppressed the in vivo proliferation of the cancer cells in the mice. Furthermore, it was found that the antibody exhibited an antibody-dependent cell-mediated cytotoxicity activity (ADCC activity) on the cancer cells. These findings have led to the completion of the present invention. To be more specific, the present invent ion provides the following <1> to <10>.

<1> An antibody capable of binding to isoleucine at position 117 of a human HB-EGF protein shown in SEQ ID NO: 1.

<2> The antibody according to <1>, which is further capable of binding to phenylalanine at position 115, glycine at position 140, glutamic acid at position 141, and arginine at position 142 of the human HB-EGF protein shown in SEQ ID NO: 1.

<3> An antibody capable of binding to human HB-EGF, the antibody having any one of the following features (a) and (b):

(a) comprising
  a light chain variable region including the amino acid sequences of SEQ ID NOs: 2 to 4 or the amino acid sequences in at least any one of which one or more amino acids are substituted, deleted, added, and/or inserted, and
  a heavy chain variable region including the amino acid sequences of SEQ ID NOs: 6 to 8 or the amino acid sequences in at least any one of which one or more amino acids are substituted, deleted, added, and/or inserted; and (b) comprising
  a light chain variable region including the amino acid sequences of SEQ ID NOs: 10 to 12 or the amino acid sequences in at least any one of which one or more amino acids are substituted, deleted, added, and/or inserted, and
  a heavy chain variable region including the amino acid sequences of SEQ ID NOs: 14 to 16 or the amino acid sequences in at least any one of which one or more amino acids are substituted, deleted, added, and/or inserted.

<4> An antibody capable of binding to human HB-EGF, the antibody having any one of the following features (a) and (b):
  (a) comprising
    a light chain variable region including the amino acid sequence of SEQ ID NO: 5 or the amino ac id sequence in which one or more amino acids are substituted, deleted, added, and/or inserted, and
    a heavy chain variable region including the amino acid sequence of SEQ ID NO: 9 or the amino acid sequence in which one or more amino acids are substituted, deleted, added, and/or inserted; and
  (b) comprising
    a light chain variable region including the amino acid sequence of SEQ ID NO: 13 or the amino acid sequence in which one or more amino acids are substituted, deleted, added, and/or inserted, and
    a heavy chain variable region including the amino acid sequence of SEQ ID NO: 17 or the amino acid sequence in which one or more amino acids are substituted, deleted, added, and/or inserted.
<5> An antibody capable of binding to human HB-EGF, the antibody comprising
    a light chain variable region including the amino acid sequence of SEQ ID NO: 18 or the amino acid sequence in which one or more amino acids are substituted, deleted, added, and/or inserted, and
    a heavy chain variable region including the amino acid sequence of SEQ ID NO: 19 or the amino acid sequence in which one or more amino acids are substituted, deleted, added, and/or inserted.
<6> A DNA encoding the antibody according to any one of <1> to <5>.
<7> A hybridoma which produces the antibody according to any one of <1> to <5>, or comprises the DNA according to <6>.
<8> A composition for treating or preventing a cancer, the composition comprising the antibody according to any one of <1> to <5> as an active ingredient.
<9> A method for using the composition according to <8> as a pharmaceutical agent.
<10> A method for treating a cancer patient by administering the composition according to <8> to the cancer patient.

Note that: the amino acid sequences of SEQ ID NOs: 2 to 4 are respectively amino acid sequences of CDRs 1 to 3 of the light chain variable region of the 35-1 antibody; the amino acid sequence of SEQ ID NO: 5 is an amino acid sequence of the light chain variable region of the 35-1 antibody; the amino acid sequences of SEQ ID NOs: 6 to 8 are respectively amino acid sequences of CDRs 1 to 3 of the heavy chain variable region of the 35-1 antibody; and the amino acid sequence of SEQ ID NO: 9 is an amino acid sequence of the heavy chain variable region of the 35-1 antibody. The amino acid sequence of SEQ ID NO: 18 is an amino acid sequence of the light chain variable region of the 35-1 humanized antibody; and the amino acid sequence of SEQ ID NO: 19 is an amino acid sequence of the heavy chain variable region of the 35-1 humanized antibody. The amino acid sequences of SEQ ID NOs: 10 to 12 are respectively amino acid sequences of CDRs 1 to 3 of the light chain variable region of the 292 antibody; the amino acid sequence of SEQ ID NO: 13 is an amino acid sequence of the light chain variable region of the 292 antibody; the amino acid sequences of SEQ ID NOs: 14 to 16 are respectively amino acid sequences of CDRs 1 to 3 of the heavy chain variable region of the 292 antibody; and the amino acid sequence of SEQ ID NO: 17 is an amino acid sequence of the heavy chain variable region of the 292 antibody.

Advantageous Effects of Invention

The present invention makes it possible to provide an antibody capable of binding to human HB-EGF, thereby inhibiting cleavage of the human HB-EGF and inhibiting binding between the human HB-EGF and an EGF receptor.

BRIEF DESCRIPTION OF DRAWINGS

FIG. 7 shows photographs for illustrating the result of analyzing the antibodies of the present invention (the 35-1 antibody and the 292 antibody) by western blot for the activity of suppressing the EGFR phosphorylation that would be induced by the human HB-EGF protein.

Figure 8:
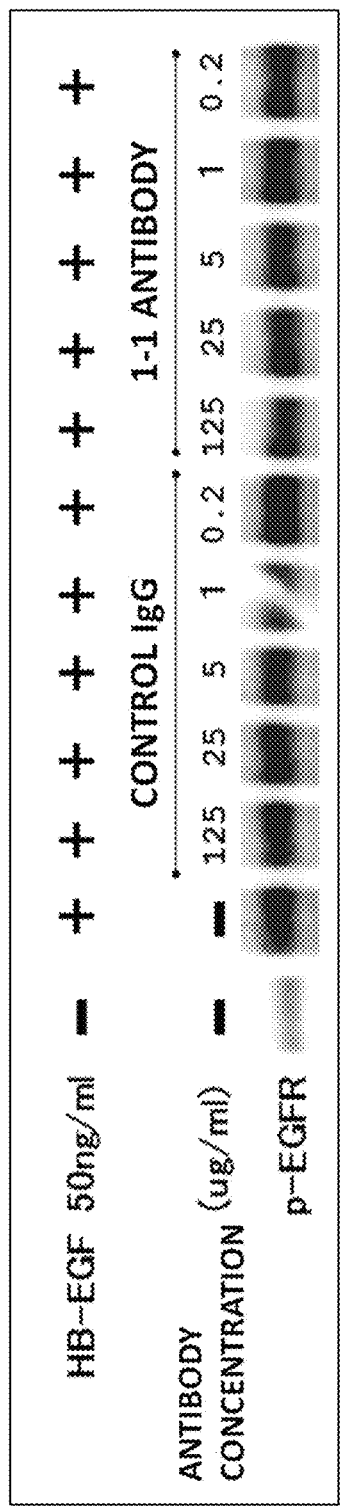

FIG. 8 shows photographs for illustrating the result of analyzing the antibody against a human HB-EGF protein (1-1 antibody) by western blot for the activity of suppressing the EGFR phosphorylation that would be induced by the human HB-EGF protein.

Figure 9:
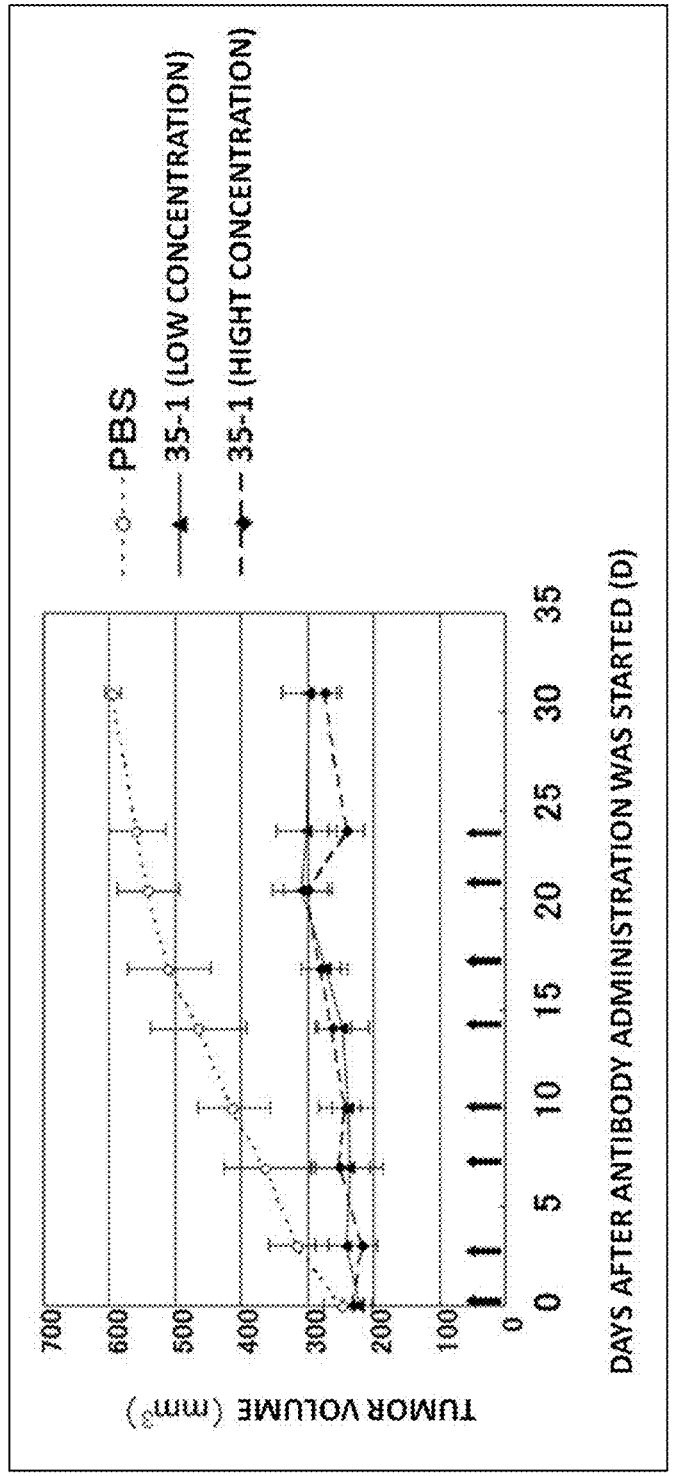

FIG. 9 is a graph for illustrating changes over time in the tumor volume in xenograft mice to which a chimerized 35-1 antibody was administered. In the figure, "35-1 (high concentration)" illustrates the result of administering an antibody solution having been diluted with PBS to 750 μg/ml, "35-1 (low concentration)" illustrates the result of administering the antibody solution having been diluted with PBS to 150 μg/ml, and "PBS" illustrates the result of administering only PBS (negative control).

Figure 10:
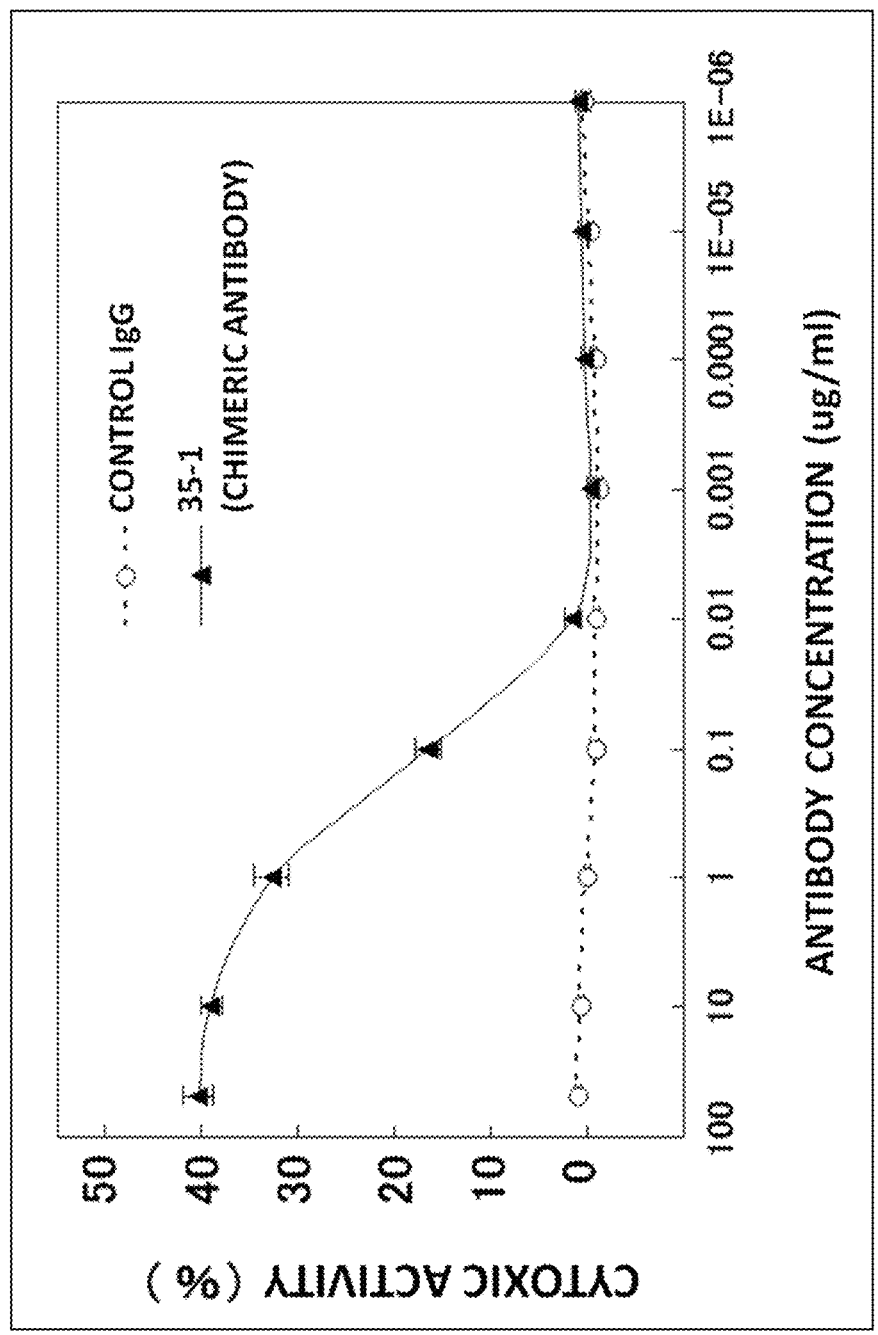

FIG. 10 is a graph for illustrating the result of analyzing the antibody-dependent cell-mediated cytotoxicity activity (ADCC activity) of the chimerized 35-1 antibody.

Figure 11:
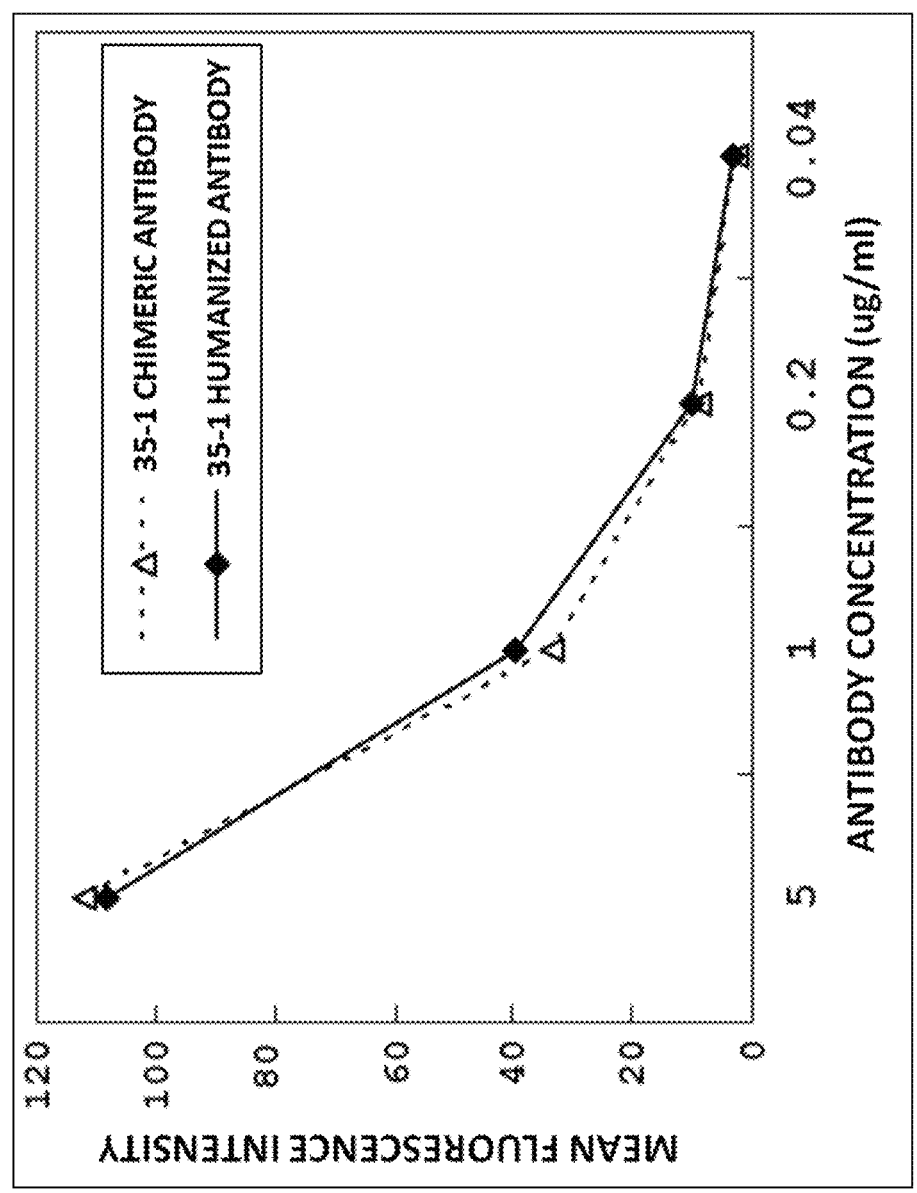

FIG. 11 is a graph for illustrating the result of analyzing, by ELISA, the reactivities of the chimerized 35-1 antibody (35-1 chimeric antibody) and a humanized 35-1 antibody (35-1 humanized antibody) with the human HB-EGF protein. In the figure, the vertical axis represents the reactivity between the antibody and the human HB-EGF protein (mean fluorescence intensity).

DESCRIPTION OF EMBODIMENTS

As described later in Examples, the present inventors have obtained two types of antibodies (35-1 antibody and 292 antibody) capable of binding to phenylalanine at position 115, isoleucine at position 117, glycine at position 140, glutamic acid at position 141, and arginine at position 142 of a human HB-EGF protein. Further, the inventors have also found that these antibodies have a strong activity of suppressing cleavage of the human HB-EGF protein (cleavage inhibitory activity), and a strong activity of suppressing EGFR phosphorylation that would occur when the human HB-EGF binds to the EGFR (neutralizing activity). On the other hand, it has also been found that an antibody against the human HB-EGF protein which does not bind to isoleucine at position 117 of the human HB-EGF protein (such as a 1-1 antibody to be described later) does not have a neutralizing activity. Thus, the present invention provides an antibody capable of binding to isoleucine at position 117 of a human HB-EGF protein.

The antibody may be an antibody capable of binding to different amino acids from the isoleucine at position 117 of the human HB-EGF protein, and is preferably an antibody capable of binding to phenylalanine at position 115, isoleucine at position 117, glycine at position 140, glutamic acid at position 141, and arginine at position 142 of the human HB-EGF protein.

In the present invention, the term "antibody" includes all classes and subclasses of immunoglobulins. An "antibody" includes a polyclonal antibody and a monoclonal antibody, and is also meant to include the form of a functional fragment of an antibody. A "polyclonal antibody" is an antibody preparation including different antibodies against different epitopes. A "monoclonal antibody" means an antibody (including an antibody fragment) obtained from a substantially uniform antibody population, and capable of recognizing a single determinant on an antigen. The antibody of the present invention is preferably a monoclonal antibody. Moreover, the antibody of the present invention is an antibody separated and/or recovered (i.e., isolated) from components in a natural environment.

In the present invention, "HB-EGF" is a protein also referred to as a heparin-binding epidermal growth factor-like growth factor, DTR (diphtheria toxin receptor), DTS, DTSF, HEGFL, and so forth. The human HB-EGF protein is typically a protein having the amino acid sequence of SEQ ID NO: 1 (the protein is specified under RefSeq ID: NP_001936, and the protein is encoded by a base sequence specified under RefSeq ID: NM_001945).

Moreover, the human HB-EGF protein may exist in a form having some amino acid naturally mutated, besides one having a typical amino acid sequence as described above. Thus, the human HB-EGF protein according to the present invention includes the protein having the amino acid sequence of SEQ ID NO: 1 in which one or more amino acids are substituted, deleted, inserted, or added. Generally, 10 amino acids or less (for example, 5 amino acids or less, 3 amino acids or less, 1 amino acid) in the amino acid sequence are substituted, deleted, inserted, or added.

Note that those skilled in the art can evaluate whether or not an antibody is the antibody capable of binding to isoleucine at position 117 and the like of the human HB-EGF protein (whether or not an antibody recognizes isoleucine at position 117 and the like of the human HB-EGF protein) by utilizing an immunological analysis method (such as flow cytometry, ELISA, western blot, immunoprecipitation) as described later in Example 3.

Further, a site containing the amino acid(s) to which the antibody of the present invention binds, that is, "epitope", means an antigen determinant present in the human HB-EGF protein (a site on the antigen where an antigen-binding domain in the antibody binds). Thus, in the present invention, the epitope may be a polypeptide (linear epitope) having several consecutive amino acids in a primary sequence of amino acids, or may be a polypeptide (discontinuous epitope, conformational epitope) formed of amino acids which are not next to each other in a primary sequence of amino acids, but which come near each other in a three-dimensional conformation by folding or the like of a peptide or protein. Moreover, such an epitope typically has at least one amino acid, most usually at least 5 amino acids (for example, 8 to 10, 6 to 20).

The "cleavage of the human HB-EGF protein" to be suppressed by the antibody of the present invention means cleavage of the human HB-EGF protein in a juxtamembrane domain thereof by a protease such as ADAM12 activated by PMA or the like. The juxtamembrane domain is typically a region having amino acids at positions 145 to 161 from the N-terminus of RefSeq ID: NP_001936. Additionally, the activity of suppressing such cleavage can be evaluated, for example, by a method described later in Example 4.

In the "binding between the human HB-EGF and the EGF receptor" to be suppressed by the antibody of the present invention, the term "human HB-EGF" is meant to include not only the full-length human HB-EGF protein (transmembrane HB-EGF), but also a partial protein (soluble HB-EGF) released extracellularly by the cleavage. An example of the soluble HB-EGF includes a protein having the amino acid sequence at positions 1 to 149 from the N-terminus of SEQ ID NO: 1. An example of HB-EGF-CTF includes a protein having the amino acid sequence at positions 150 to 208 from the N-terminus of SEQ ID NO: 1. In addition, the "EGF receptor" according to the present invention is EGFR (ErbB1) or ErbB4.

Further, the "binding between the human HB-EGF and the EGF receptor" to be suppressed by the antibody of the present invention is meant to include not only the binding between the human HB-EGF and the EGF receptor, but also change in the structure of EGFR or ErbB4 attributable to the binding, homodimerization or heterodimerization of EGFR or ErbB4 induced by the structural change, phosphorylation of EGFR or ErbB4 attributable to the dimerization, activation of the MAPK pathway elicited by the phosphorylation, and activation of the PI3K-Akt pathway elicited by the phosphorylation. A target to be suppressed by the antibody of the present invention is preferably the phosphorylation of EGFR, more preferably phosphorylation of EGFR in a cancer cell. Additionally, the activity of suppressing such phosphorylation can be evaluated, for example, by a method described later in Example 5.

Moreover, the antibody of the present invention preferably has an activity of suppressing cell proliferation (cell-proliferation suppressing activity) or an antibody-dependent cell-mediated cytotoxicity activity (ADCC activity), in addition to the above-described activity of suppressing cleavage of the human HB-EGF protein (cleavage inhibitory activity) and activity of suppressing the binding between the human HB-EGF and the EGF receptor (neutralizing activity), and more preferably has a cleavage inhibitory activity, a neutralizing activity, a cell-proliferation suppressing activity, and an ADCC activity.

In the present invention, the phrase "suppressing cell proliferation" is meant to include not only suppression of cell proliferation (cell division) per se, but also suppression of cell proliferation by inducing cell death (such as apoptosis). A target to be suppressed by the antibody of the present invention is preferably cancer cell proliferation, more preferably in vivo cancer cell proliferation (increase in tumor). The activity of suppressing such in vivo tumor proliferation can be evaluated, for example, by a method described later in Example 6. A preferable embodiment of the antibody of the present invention is an antibody capable of reducing a tumor volume to 230% or less (for example, 220% or less, 210% or less, 200% or less, 190% or less, 180% or less, 170% or less) 30 days after the antibody administration is started according to the method, provided that a tumor volume at the time when the antibody administration is started is taken as 100%.

Further, a cytotoxic target by the antibody of the present invention is preferably cancer cells. The ADCC activity on such cancer cells can be evaluated, for example, by a method described later in Example 7. A preferable embodiment of the antibody of the present invention is an antibody having an ADCC activity of 10% or more (for example, 20% or more, 30% or more) when added to target cells at a concentration of 1 µg/ml according to the method.

The type of cancer as a target of the proliferation suppression and/or cytotoxic target by the antibody of the present invention is not particularly limited because associations between HB-EGF and various cancers have been revealed as described in NPLs 7 to 11 and 17 to 21, for example.

Another preferable embodiment of the antibody of the present invention includes an antibody capable of binding to human HB-EGF, the antibody having any one of the following features (a) and (b):
(a) comprising
a light chain variable region including the amino acid sequences of SEQ ID NOs: 2 to 4 (amino acid sequences of CDRs 1 to 3 of a light chain variable region of the 35-1 antibody to be described later) or the amino acid sequences in at least any one of which one or more amino acids are substituted, deleted, added, and/or inserted, and
a heavy chain variable region including the amino acid sequences of SEQ ID NOs: 6 to 8 (amino acid sequences of CDRs 1 to 3 of a heavy chain variable region of the 35-1 antibody to be described later) or the amino acid sequences in at least any one of which one or more amino acids are substituted, deleted, added, and/or inserted; and
(b) comprising
a light chain variable region including the amino acid sequences of SEQ ID NOs: 10 to 12 (amino acid sequences of CDRs 1 to 3 of a light chain variable region of the 292 antibody to be described later) or the amino acid sequences in at least any one of which one or more amino acids are substituted, deleted, added, and/or inserted, and
a heavy chain variable region including the amino acid sequences of SEQ ID NOs: 14 to 16 (amino acid sequences of CDRs 1 to 3 of a heavy chain variable region of the 292 antibody to be described later) or the amino acid sequences in at least any one of which one or more amino acids are substituted, deleted, added, and/or inserted.

Another more preferable embodiment of the antibody of the present invention includes an antibody capable of binding to human HB-EGF, the antibody having any one of the following features (a) and (b):
(a) comprising
a light chain variable region including the amino acid sequence of SEQ ID NO: 5 (an amino acid sequence of the light chain variable region of the 35-1 antibody to be described later) or the amino acid sequence in which one or more amino acids are substituted, deleted, added, and/or inserted, and
a heavy chain variable region including the amino acid sequence of SEQ ID NO: 9 (an amino acid sequence of the heavy chain variable region of the 35-1 antibody to be described later) or the amino acid sequence in which one or more amino acids are substituted, deleted, added, and/or inserted; and
(b) comprising
a light chain variable region including the amino acid sequence of SEQ ID NO: 13 (an amino acid sequence of the light chain variable region of the 292 antibody to be described later) or the amino acid sequence in which one or more amino acids are substituted, deleted, added, and/or inserted, and
a heavy chain variable region including the amino acid sequence of SEQ ID NO: 17 (an amino acid sequence of the heavy chain variable region of the 292 antibody to be described later) or the amino acid sequence in which one or more amino acids are substituted, deleted, added, and/or inserted.

The antibody of the present invention includes a mouse antibody, a chimeric antibody, a humanized antibody, a human antibody, and a functional fragment of these antibodies. For administration as a pharmaceutical agent to human, the antibody of the present invention is desirably a chimeric antibody, a humanized antibody, or a human antibody from the viewpoint of side effect reduction. A preferable embodiment of the humanized antibody of the present invention includes an antibody capable of binding to human HB-EGF, the antibody comprising a light chain variable region including the amino acid sequence of SEQ ID NO: 18 or the amino acid sequence in which one or more amino acids are substituted, deleted, added, and/or inserted, and a heavy chain variable region including the amino acid sequence of SEQ ID NO: 19 or the amino acid sequence in which one or more amino acids are substituted, deleted, added, and/or inserted.

In the present invention, a "chimeric antibody" is an antibody obtained by linking a variable region of an antibody of one species to a constant region of an antibody of another species. A chimeric antibody can be obtained as follows, for example. Concretely, a mouse is immunized with an antigen. A portion corresponding to an antibody variable part (variable region) which binds to the antigen is cut out from a gene of a monoclonal antibody of the mouse. The portion is linked to a gene of a constant part (constant region) of an antibody derived from human bone marrow. This is incorporated into an expression vector, which is then introduced into a host for the production of a chimeric antibody (for example, Japanese Unexamined Patent Application Publication No. Hei 8-280387, U.S. Pat. Nos. 4,816,397, 4,816,567, and 5,807,715). Moreover, in the present invention, a "humanized antibody" is an antibody obtained by grafting (CDR grafting) a gene sequence of an antigen-binding site (CDR) of a non-human-derived antibody onto a human antibody gene. The preparation methods are known (see, for example, EP239400, EP125023, WO90/07861, WO96/02576). In the present invention, a "human antibody" is an antibody all regions of which are derived from human. In preparing a human antibody, it is possible to utilize a screening method for a production of an active antibody by human B cells, a phage display method, a transgenic animal (for example, a mouse) capable of producing a repertoire of the human antibody by immunization, or other means. Preparation methods for a human antibody are known (for example, Nature, 362: 255-258 (1993), Intern. Rev. Immunol, 13: 65-93 (1995), J. Mol. Biol, 222: 581-597 (1991), Nature Genetics, 15: 146-156 (1997), Proc. Natl. Acad. Sci. USA, 97: 722-727 (2000), Japanese Unexamined Patent Application Publication Nos. Hei 10-146194 and Hei 10-155492, Japanese Patent No. 2938569, Japanese Unexamined Patent Application Publication No. Hei 11-206387, International Application Japanese-Phase Publication Nos. Hei 8-509612 and Hei 11-505107).

In the present invention, a "functional fragment" of an antibody means apart (partial fragment) of an antibody, which binds to the antigen. Examples of the form of the "functional fragment" of the antibody according to the present invention include Fab, Fab', F(ab') 2, a variable region fragment (Fv), a disulfide bonded Fv, a single chain Fv (scFv), a sc (Fv) 2, a diabody, a polyspecific antibody, and polymers thereof.

Here, "Fab" means a monovalent antigen-binding fragment, of an immunoglobulin, composed of a part of one light chain and a part of one heavy chain. Fab can be obtained by papain digestion of an antibody or by a recombination method. "Fab'" is different from Fab in that a small number of residues are added to the carboxy terminus of a heavy chain CH1 domain including one or more cysteines from an antibody hinge region. "F(ab')2" means a bivalent antigen-binding fragment, of an immunoglobulin, composed of parts of both light chains and parts of both heavy chains.

A "variable region fragment (Fv)" is a smallest antibody fragment having complete antigen recognition and binding sites. An Fv is a dimer in which a heavy chain variable region and a light chain variable region are strongly linked by non-covalent bonding. A "single chain Fv (scFv)" includes a heavy chain variable region and a light chain variable region of an antibody, and these regions exist in a single polypeptide chain. A "sc(Fv)2" is a single chain obtained by linking two heavy chain variable regions and two light chain variable regions with a linker or the like. A "diabody" is a small antibody fragment having two antigen-binding sites. This fragment includes a heavy chain variable region linked to a light chain variable region in a single polypeptide chain. Each region forms a pair with a complementary region in another chain. A "polyspecific antibody" is a monoclonal antibody having a binding specificity to at least two different antigens. For example, a polyspecific antibody can be prepared by coexpression of two immunoglobulin heavy chain/light chain pairs in which two heavy chains have different specificities.

The antibody of the present invention includes antibodies whose amino acid sequences are modified without impairing desirable activities (antigen binding activity, the cleavage inhibitory activity, the neutralizing activity, and other biological properties). An amino acid sequence mutant of the antibody of the present invention can be prepared by introduction of a mutation into a DNA encoding an antibody chain of the present invention or by peptide synthesis. Examples of such a modification include substitution, deletion, addition, and/or insertion of a residue in the amino acid sequence of the antibody of the present invention. A site where the amino acid sequence of the antibody is modified may be a constant region of the heavy chain or the light chain of the antibody or a variable region (framework region and CDR) thereof, as long as the resulting antibody has activities equivalent to those before the modification. It is conceivable that modification on an amino acid other than CDR has a relatively small influence on binding affinity for an antigen. As of now, there are known screening methods for an antibody whose affinity for an antigen has been enhanced by modifying an amino acid of CDR (PNAS, 102: 8466-8471 (2005), Protein Engineering, Design & Selection, 21: 485-493 (2008), International Publication No. WO2002/051870, J. Biol. Chem., 280: 24880-24887 (2005), Protein Engineering, Design & Selection, 21: 345-351 (2008)).

The number of amino acids modified is preferably 10 amino acids or less, more preferably 5 amino acids or less, and most preferably 3 amino acids or less (for example, 2 amino acids or less, 1 amino acid). The modification of amino acids is preferably conservative substitution. In the present invention, the term "conservative substitution" means substitution with a different amino acid residue having a chemically similar side chain. Groups of amino acid residues having chemically similar amino acid side chains are well known in the technical field to which the present invention pertains. For example, amino acids can be grouped into acidic amino acids (aspartic acid and glutamic acid), basic amino acids (lysine, arginine, histidine), and neutral amino acids such as amino acids having a hydrocarbon chain (glycine, alanine, valine, leucine, isoleucine, proline), amino acids having a hydroxy group (serine, threonine), amino acids containing sulfur (cysteine, methionine), amino acids having an amide group (asparagine, glutamine), an amino acid having an imino group (proline), and amino acids having an aromatic group (phenylalanine, tyrosine, tryptophan).

Meanwhile, "having equivalent activities" or similar phrases mean that the antigen binding activity, the cleavage activity, or the neutralizing activity is equivalent (for example, 70% or more, preferably 80% or more, more preferably 90% or more) to that of a subject antibody (typically, the 35-1 antibody or the 292 antibody described later in Examples). The antigen binding activity can be evaluated, for example, by analyzing the reactivity with an antigen by ELISA, or preparing cells expressing an antigen and then analyzing the reactivity with an antibody sample using a flow cytometer, as described later in Examples. The cleavage activity can be evaluated, for example, based on the percentage of transmembrane HB-EGF remaining on the cell surface stimulated with PMA or based on the percentage of HB-EGF-CTF formed on the cell surface stimulated with PMA, by a method described later in Examples. Moreover, the neutralizing activity can be evaluated based on the degree of the phosphorylation of an EGFR protein in a cancer cell stimulated with an HB-EGF protein.

Further, the modification on the antibody of the present invention may be a modification on post-translational process of the antibody such as, for example, alternation of the number or position of the glycosylation sites. Thereby, for example, the ADCC activity of the antibody can be improved. Glycosylation of the antibody is typically N-linked or O-linked glycosylation. The glycosylation of the antibody largely depends on host cells used for expression of the antibody. The glycosylation pattern can be modified by known methods such as introduction or deletion of a certain enzyme involved in carbohydrate production (Japanese Unexamined Patent Application Publication No. 2008-113663, U.S. Pat. Nos. 5,047,335, 5,510,261, and 5,278,299, International Publication No. WO99/54342). Furthermore, in the present invention, for the purpose of increasing the stability of the antibody or other purposes, an amino acid subjected to deamidation or an amino acid next to the amino acid subjected to the deamidation may be substituted with a different amino acid to suppress the deamidation. Alternatively, the stability of the antibody can also be increased by substituting glutamic acid with a different amino acid. The present invention also provides an antibody thus stabilized.

In the case where the antibody of the present invention is a polyclonal antibody, the polyclonal antibody can be obtained as follows. Concretely, an animal is immunized with an antigen (the human HB-EGF protein, a partial peptide thereof (for example, an EGF domain of the human HB-EGF protein), cells expressing these, or the like). An antiserum from the animal is purified by conventional means (for example, salting-out, centrifugation, dialysis, column chromatography, or the like) to obtain the polyclonal antibody.

Meanwhile, a monoclonal antibody can be prepared by a hybridoma method or a recombinant DNA method.

The hybridoma method is typically a method by Kohler and Milstein (Kohler & Milstein, Nature, 256: 495 (1975)). Antibody-producing cells used in the cell fusion process of this method are spleen cells, lymph node cells, peripheral blood leukocytes, or the like of an animal (for example, mouse, rat, hamster, rabbit, monkey, goat, chicken, camel) immunized with the antigen. It is also possible to use antibody-producing cells obtained by causing the antigen to act, in a medium, on the above-described types of cells, lymphocytes, or the like, which are isolated from non-immunized animals in advance. As myeloma cells, various known cell lines can be used. The antibody-producing cells and the myeloma cells may be ones originated from different animal species, as long as they can be fused. However, the antibody-producing cells and the myeloma cells are preferably originated from the same animal species. Hybridomas can be produced, for example, by cell fusion between mouse myeloma cells and spleen cells obtained from a mouse immunized with the antigen. By the subsequent screening, a hybridoma which produces an antibody capable of binding to isoleucine at position 117 and the like of the human HB-EGF protein can be obtained. A monoclonal antibody capable of binding to isoleucine at position 117 and the like of the human HB-EGF protein can be obtained by culturing the hybridoma, or from the ascites of a mammal to which the hybridoma is administered.

The recombinant DNA method is a method by which the antibody of the present invention is produced as a recombinant antibody as follows. A DNA encoding the antibody of the present invention is cloned from a hybridoma, B cells, or the like. The cloned DNA is incorporated into an appropriate vector, which is then introduced into host cells (for example, a mammalian cell line, *Escherichia coli*, yeast cells, insect cells, plant cells, or the like) for the production (for example, P. J. Delves, Antibody Production: Essential Techniques, 1997 WILEY, P. Shepherd and C. Dean Monoclonal Antibodies, 2000 OXFORD UNIVERSITY PRESS, Vandamme A. M. et al., Eur. J. Biochem. 192: 767-775 (1990)). For the expression of the DNA encoding the antibody of the present invention, DNAs encoding the heavy chain and the light chain may be incorporated into expression vectors, respectively, to transform the host cells. Alternatively, the DNAs encoding the heavy chain and the light chain may be incorporated into a single expression vector to transform the host cells (see International Publication No. WO94/11523). The antibody of the present invention can be obtained in a substantially pure and homogeneous form by culturing the host cells, followed by separation and purification from the host cells or the culture solution. For the separation and purification of the antibody, normal methods used for polypeptide purification can be employed. When a transgenic animal (cattle, goat, sheep, pig, or the like) incorporating the antibody gene is prepared using a transgenic animal preparation technique, a large amount of monoclonal antibodies derived from the antibody gene can also be obtained from milk of the transgenic animal.

Thus, the present invention can also provide: a DNA encoding the antibody of the present invention; and a hybridoma which produces the antibody of the present invention, or comprises the DNA encoding the antibody of the present invention.

Moreover, the antibody of the present invention may comprise a compound or molecule such as a drug or prodrug binding to the antibody. Administering such an antibody allows delivering of the compound or molecule to a site (for example, cancer cells) where the human HB-EGF protein is expressed. Such a drug or prodrug is not particularly limited, but is preferably a substance having an anti-tumor activity from the viewpoint of additionally or synergistically enhancing the anti-tumor effect of the antibody of the present invention. Such a substance having an anti-tumor activity is not particularly limited, and examples thereof include anti-cancer agents (irinotecan (CPT-11), an irinotecan metabolite SN-38 (10-hydroxy-7-ethylcamptothecin), Adriamycin, Taxol; alkylating agents such as 5-fluorouracil, nimustine, and ranimustine; antimetabolites such as gemcitabine and hydroxycarbamide; plant alkaloids such as etoposide and vincristine; anticancer antibiotics such as mitomycins and bleomycin; platinum preparations such as cisplatin; agents for molecularly targeted therapy such as sorafenib and erlotinib; methotrexate, cytosine arabinoside, 6-thioguanine, 6-mercaptopurine, cyclophosphamide, ifosfamide, busulfan, and the like. Additionally, radioisotopes can also be suitably utilized as the substance having an anti-tumor activity which binds to the antibody of the present invention.

Further, it is possible to make the antibody and the compound or molecule bind to each other by methods known in the technical field, and the binding may be any of direct binding and indirect binding. For example, in the direct binding, covalent bonding can be utilized. In the indirect binding, a linker can be utilized in the binding. Those skilled in the art can make the antibody and the compound or molecule bind to each other via such a linker, for example, with reference to the descriptions of: Hermanson, G. T. Bioconjugate Techniques, Academic Press, 1996; Harris, J. M. and Zalipsky, S. eds., Poly(ethylene glycol), Chemistry and Biological Applications, ACS Symposium Series, 1997; Veronese, F. and Harris, J. M. eds., Peptide and protein PEGylation. Advanced Drug Delivery Review 54 (4), 2002. The number of the compounds or molecules binding to one molecule of the antibody of the present invention is not particularly limited in theory, but is normally 1 to 10, preferably 1 to 8, from the viewpoints of the stability of a complex of the antibody with the compound or the like, ease of the production, and so forth.

Furthermore, as described later in Examples, the antibody of the present invention is capable of suppressing HB-EGF protein cleavage and EGFR phosphorylation, which are important factors in the proliferation and so forth of cancer cells. Accordingly, the antibody of the present invention can be utilized to treat or prevent a cancer. Thus, the present invention also provides: a composition for treating or preventing a cancer, the composition comprising the antibody of the present invention as an active ingredient; and a method for treating or preventing a cancer, the method comprising a step of administering a therapeutically or preventively effective amount of the antibody of the present invention to human (a method for treating a cancer patient by administering the composition to the cancer patient, and the like). Moreover, the present invention provides a method for using the composition as a pharmaceutical agent. Note that the cancer as a target of the antibody of the present invention is not particularly limited as described above, and various cancers can be targeted.

The composition for treating or preventing a cancer, which comprises the antibody of the present invention as the active ingredient, can be used in the form of a composition comprising the antibody of the present invention and any ingredient, for example, a saline, an aqueous solution of glucose, a phosphate buffer, or the like. The composition for treating or preventing a cancer of the present invention may be formulated in a liquid or lyophilized form as necessary, and may also optionally comprise a pharmaceutically acceptable carrier or medium, for example, a stabilizer, a preservative, an isotonic agent, or the like.

Examples of the pharmaceutically acceptable carrier include: mannitol, lactose, saccharose, human albumin, and the like for a lyophilized preparation; and a saline, water for injection, a phosphate buffer, aluminium hydroxide, and the like for a liquid preparation. However, the examples are not limited thereto.

The method for administering the composition for treating or preventing a cancer of the present invention differs depending on the age, weight, sex, and health state, of an administration target, and the like. The administration can be carried out by any administration route: oral administration and parenteral administration (for example, intravenous administration, intraarterial administration, local administration). The dose of the composition may vary depending on the age, weight, sex, and health state of a patient, the degree of the progression of the cancer, and ingredients of the composition to be administered. Nevertheless, the dose is generally 0.01 to 1000 mg, preferably 1 to 100 mg, per kg body weight for an adult per day in the case of intravenous administration.

In the method for treating or preventing a cancer of the present invention, the method for administering the antibody of the present invention is not particularly limited as described above, and the administration can be carried out by any administration route: oral administration and parenteral administration. Those skilled in the art can achieve the administration of the composition in a form appropriate therefor by selecting the pharmaceutically acceptable carrier or medium, and so forth. Those skilled in the art can determine the therapeutically or preventively "effective amount" of the antibody of the present invention to be administered to human, by taking the age, weight, sex, and health state of a patient, the degree of the progression of the cancer, the administration route, and the like into consideration as described above. Moreover, the "human" as the administration target of the antibody of the present invention is not particularly limited, and an example thereof includes a person having a cancer (cancer patient). Alternatively, from the viewpoints of preventing and reducing cancer recurrence, the "human" may be a person from whom a cancer has been removed by a chemotherapy, radiation therapy, surgical therapy, or the like.

The method for treating or preventing a cancer of the present invention may further comprise, in addition to the step of administering the antibody of the present invention, a step of evaluating effectiveness of the antibody of the present invention. To be more specific, the present invention provides a method for treating or preventing a cancer, the method comprising the steps of:

administering a therapeutically or preventively effective amount of the antibody of the present invention to human; and evaluating effectiveness of the antibody of the present invention in the human after the administration.

The "evaluating effectiveness" of the antibody of the present invention is not particularly limited. For example, it can be determined that the antibody of the present invention is effective in a cancer treatment or the like, if the tumor size, the metastatic ability of the cancer, or expressions of various cancer markers after the administration are lower than those before the administration. Moreover, the effectiveness of the antibody of the present invention can also be evaluated based on abnormalities due to a cancer, for example, weight reduction, stomachache, back pain, reduced appetite, nausea, vomiting, systemic malaise, weakness, jaundice, and the like. Further, in a case where a tumor tissue is excised after the treatment with the antibody of the present invention, the tumor tissue may be examined for the degree of signal transduction in which HB-EGF is involved, in order to determine that the antibody of the present invention is effective in the cancer treatment or the like. For example, when it is detected that phosphorylation of EGFR, which is normally enhanced in a tumor tissue, is inhibited by administering the antibody of the present invention, it can be determined that the antibody of the present invention is effective in the cancer treatment or the like.

As described above, HB-EGF protein expression enhancement and the like have been recognized in various cancers. Accordingly, the antibody of the present invention is conceivably applicable not only to the treatment and prevention of a cancer but also to testing for a cancer. Particularly, since an EGF domain where the epitope for the antibody of the present invention is present is located in an extracellular region of an HB-EGF protein, cancer cells expressing the HB-EGF protein can be easily and efficiently detected by cell immunostaining, flow cytometry, or the like. The present invention also provides a testing agent and a kit for a cancer, which comprises the antibody of the present invention as an active ingredient.

When the antibody of the present invention is used in the testing for a cancer or used in the detection of a tumor site in treating the cancer, the antibody of the present invention may be labeled. As the label, it is possible to use, for example, a radioactive substance, a fluorescent dye, a chemiluminescent substance, an enzyme, or a coenzyme. When the antibody of the present invention is to be prepared as a testing agent, it can be obtained in any dosage form by adopting any means suitable for the purpose. For example, a purified antibody is measured for the antibody titer and diluted as appropriate with PBS or the like; thereafter, 0.1% sodium azide or the like can be added as a preservative. Alternatively, for example, the antibody of the present invention adsorbed to latex or the like is measured for the antibody titer and diluted as appropriate, and a preservative may be added thereto for use.

Additionally, the present invention also comprises a kit for detecting a cancer, the kit comprising the testing agent of the present invention as a constituent. The kit may comprise, for example, for carrying out an antigen-antibody reaction (such as an ELISA method, an immunohistochemical staining method, flow cytometry), various reagents (such as a secondary antibody, a chromogenic reagent, a staining reagent, a buffer, a standard preparation), a reaction vessel, an operation tool, and/or an instruction, in addition to the testing agent of the present invention.

EXAMPLES

Hereinafter, the present invention will be more specifically described based on Examples. However, the present invention is not limited to the following Examples. In addition, in the present Examples, unless otherwise specifically stated, "HB-EGF" refers to a human-derived transmembrane HB-EGF protein having an amino acid sequence (amino acids at positions 1 to 208) of SEQ ID NO: 1 (NCBI Reference Sequence: NP_001936). Moreover, "soluble HB-EGF" refers to a partial protein of HB-EGF released extracellularly by protease cleavage (shedding), and "HB-EGF-CTF (HB-EGF C-terminal fragment)" refers to a partial protein remaining at the cell membrane side after the cleavage. Note that, in HB-EGF, an EGF domain is a region having amino acids at positions 107 to 144 from the N-terminus, a juxtamembrane domain (shed region) is a region having amino acids at positions 145 to 161 from the N-terminus, an extracellular region is a region having amino acids at positions 1 to 161 from the N-terminus, and a transmembrane (transmembrane domain) is a region having amino acids at positions 162 to 183 from the N-terminus.

Example 1

Antibodies against a human HB-EGF protein were prepared by the following method.

<Acquisition of HB-EGF cDNA>

From a cDNA library prepared from human pancreatic cancer cells AsPC-1 (ATCC, catalog number: CRL-1682), a DNA encoding a human HB-EGF protein (protein having the amino acid sequence at positions 1 to 208 of SEQ ID NO: 1) was amplified by a PCR method. The obtained PCR product was cloned in a T7Blue T-vector (manufactured by Novagen Inc., catalog number: 69820), and the base sequence was confirmed. Moreover, the vector obtained in this manner was designated as hHB-EGF-pT7.

<Preparation of Cells Expressing Transmembrane HB-EGF>

Animal cells stably expressing the full length of the human HB-EGF protein were prepared as follows. To be more specific, first, an end of a DNA amplified by the PCR method using the hHB-EGF-pT7 as a template was cleaved with NotI and BamHI, and inserted into a NotI-BamHI site of an animal cell expression vector. As the animal cell expression vector, pQCxmhIPG was used which was controlled by a CMV promoter, and which simultaneously expressed a target gene and a puromycin-EGFP fusion protein by an IRES sequence. The pQCxmhIPG is a vector modified by the present inventors from pQCXIP Retroviral Vector of "BD Retro-X Q Vectors" (manufactured by Clontech Laboratories, Inc., catalog number: 631516). The prepared vector was designated as HB-EGF-pQCxmhIPG.

Moreover, in order to confirm the expression of recombinant HB-EGF molecules on the cell membrane, HA-HB-EGF was prepared in which an HA tag was added between amino acids at positions 24 and 25 from the N-terminus by an overlap extension PCR method. Then, the HA-HB-EGF was also inserted into the pQCxmhIPG as described above. The vector thus prepared was designated as HA-HB-EGF-pQCxmhIPG.

Next, the prepared vector was introduced into 293T cells or CHO-K1 cells using Pantropic Retroviral Express ion System (manufactured by Clontech Laboratories, Inc., catalog number: K1063-1) as follows.

First, GP2-293 (manufactured by Clontech Laboratories, Inc., catalog number: K1063-1) in an 80 to 90% confluent state was prepared on a collagen-coated 100-mm dish, into which 11.2 μg of the expression vector (HB-EGF-pQCxmhIPG or HA-HB-EGF-pQCxmhIPG) constructed as described above and 11.2 μg of pVSV-G (manufactured by Clontech Laboratories, Inc., catalog number: K1063-1) were co-introduced using Lipofectamine 2000 (manufactured by Invitrogen Corporation, catalog number: 11668-019). After 48 hours, the supernatant containing virus particles was collected, and the virus particles were precipitated by ultracentrifugation (18,000 rpm, 1.5 hours, 4° C.). The precipitate was suspended in 30 μL of THE (50 mM Tris-HCl [pH=7.8], 130 mM NaCl, 1 mM EDTA). Thereby, a retroviral vector concentrate liquid was prepared. Then, 5 μl of the retroviral vector concentrate liquid was diluted with 150 μL of DMEM (manufactured by SIGMA-ALDRICH CO., catalog number; D5796)-10% FBS containing 8 μg/mL of hexadimethrine bromide (manufactured by SIGMA-ALDRICH CO., catalog number: H-9268). Thereby, a virus-particle containing medium was prepared.

Next, the cells were prepared to an approximately 40% confluent state on a 96-well microplate, and the medium of these cells was replaced with the virus-particle containing medium. Then, these cells were cultured using a selective medium containing puromycin (manufactured by SIGMA-ALDRICH CO., catalog number: P-8833). Thus, cells expressing the target gene (HB-EGF/st293T, HA-HB-EGF/st293T, HB-EGF/stCHO-K1, HA-HB-EGF/stCHO-K1) were obtained. Note that the 293T cells were cultured using a medium containing 5 μg/mL of puromycin, and the CHO-K1 cells were cultured using a selective medium containing 10 μg/mL of puromycin.

<Preparation of Cells Secreting and Expressing Partial-Length HB-EGF>

Animal cells expressing soluble HB-EGF (protein having the amino acid sequence at positions 1 to 149 from the N-terminus of SEQ ID NO: 1) or an HB-EGF extracellular region (protein having the amino acid sequence at positions 1 to 161 from the N-terminus of SEQ ID NO: 1) were prepared as follows.

An end of a DNA of partial-length HB-EGF amplified by the PCR method using the hHB-EGF-pT7 as a template was cleaved with NotI and BamHI, and inserted into a NotI-BamHI site of an animal cell secretory expression vector pQCxmhIPG. The vector in which a DNA encoding the soluble HB-EGF (HB-EGFv5) was inserted was designated as HB-EGFv5-pQCxmhIPG, and the vector in which a DNA encoding the HB-EGF extracellular region (HB-EGFv4) was inserted was designated as HB-EGFv4-pQCxmhIPG.

Then, the prepared vectors were each introduced into 293T cells using Pantropic Retroviral Expression System as described above. The cells were cultured using a selective medium containing 5 µg/mL of puromycin. Thus, cell lines (HB-EGFv5/st293T and HB-EGFv4/st293T) each stably expressing the target gene were established.

<Preparation of Partial-Length HB-EGF Purified Proteins (Animal Cell-Derived Recombinant Proteins)>

The expression cell lines (HB-EGFv5/st293T and HB-EGFv4/st293T) established above were each cultured using 1 L of a 293 medium (product name: CD293, manufactured by Invitrogen Corporation). The culture supernatant was collected, and recombinant proteins were purified therefrom using TALON Purification Kit (manufactured by Clontech Laboratories, Inc., catalog number: K1253-1). The purified proteins (HB-EGFv5 and HB-EGFv4) were confirmed by SDS-PAGE and western blot. Further, the protein concentrations were determined using Protein Assay Kit II (manufactured by Bio-Rad Laboratories, Inc., catalog number: 500-0002JA).

<Immunization with Antigen>

The HB-EGFv4 was diluted with PBS and mixed with the same amount of a complete adjuvant (manufactured by SIGMA-ALDRICH CO., catalog number: F5881) to form an emulsion. Then, 4- to 5-week old C3H mice (manufactured by Japan SLC, Inc.) and so forth were immunized with 5 to 20 µg of the emulsion per animal 6 times at intervals of 3 to 7 days. Three days after the final immunization, lymphoid cells were extracted from the mice and fused to mouse myeloma cells P3U1 (P3-X63Ag8U1) by a method described below.

<Cell Fusion>

The cell fusion was carried out based on the following general method. FBS in all media used was inactivated by an incubation treatment at 56° C. for 30 minutes. P3U1 was cultured and thus prepared using RPMI 1640-10% FBS (containing Penicillin-Streptomycin). The extracted mouse lymphoid cells were mixed with P3U1 at a ratio of 10:1 to 2:1 and centrifuged. To the precipitated cells, 50% polyethylene glycol 4000 (manufactured by Merck KGaA, catalog number: 1.09727.0100) was gradually added and gently mixed together. Then, the mixture was centrifuged. The precipitated fusion cells were diluted as appropriate with a 15% FBS-containing HAT medium (RPMI 1640, HAT-supplement (manufactured by Invitrogen Corporation, catalog number: 11067-030), Penicillin-Streptomycin), and seeded into a 96-well microplate in an amount of 200 µL/well. The fusion cells were cultured in a $CO_2$ incubator (5% $CO_2$, 37° C.). When colonies were formed, the culture supernatant was sampled and screened as described below.

<Selection of Cells Producing Anti-HB-EGF Monoclonal Antibodies>

Hybridomas producing anti-HB-EGF antibodies were selected by the enzyme-linked immunosorbent assay (ELISA). The assay used the recombinant human HB-EGF proteins as immunogens, which had been dispensed in a 96-well ELISA plate (manufactured by nunc A/S) in an amount of 0.5 µg/mL, that is, 50 µL/well, and left to stand at room temperature for 2 hours or at 4° C. overnight for adsorption. After the solution was removed, 1% BSA (manufactured by Nacalai Tesque, Inc., catalog number: 01863-35)-5% sucrose (manufactured by WAKO PURE CHEMICAL INDUSTRIES, LTD.)—PBS was added in an amount of 150 µL/well, and left to stand at room temperature for 2 hours to block the remaining active groups. After the resultant was left to stand, the solution was removed, and the hybridoma culture supernatant was dispensed as a primary antibody in an amount of 50 µL/well and left to stand for 1 hour. After the plate was washed with 0.05% Tween 20-PBS, an HRP-labeled goat anti-mouse IgG (manufactured by MBL Co., Ltd., catalog number: 330) having been diluted to 1/10000 was added as a secondary antibody in an amount of 50 µL/well and left to stand at room temperature for 1 hour. After the plate was washed with 0.05% Tween 20-PBS, a color developing solution (5 mM sodium citrate, 0.8 mM 3.3'.5.5'-tetramethylbenzidine-2HCl, 10% N,N-dimethylformamide, 0.625% polyethylene glycol 4000, 5 mM citric acid monohydrate, 5 mM $H_2O_2$) was added thereto in an amount of 50 µL/well and left to stand at room temperature for 20 minutes to develop a color. The color development was terminated by adding 1 M phosphoric acid in an amount of 50 µL/well. Then, the absorbance at a main wavelength of 450 nm and a sub-wavelength of 620 nm was measured using a plate reader (manufactured by Thermo Fisher Scientific Inc.).

It was confirmed by the same ELISA that the hybridoma culture supernatants thus selected did not further react with other purified recombinant proteins having the same tag sequence as the recombinant proteins used as the immunogens. This confirmed that the produced antibodies recognized not the tag portion or the linker portion but HB-EGF.

Then, the hybridomas confirmed to produce an antibody specifically recognizing HB-EGF were cultured to expand using a 15% FBS-containing HT medium (RPMI 1640, HT-supplement (manufactured by Invitrogen Corporation, catalog number: 21060-017), Penicillin-Streptomycin) and subjected to monocloning by the limiting dilution method.

<Acquisition of Anti-HB-EGF Monoclonal Antibodies>

Each of the hybridomas having been subjected to the monocloning above was cultured using a serum-free medium (manufactured by GIBCO Corp., catalog number: 12300-067). From the culture supernatant, antibodies were purified by a general affinity purification method using Protein A-Sepharose. The reactivities of these antibodies with human HB-EGF were confirmed as described above by the enzyme-linked immunosorbent assay (ELISA) using the purified proteins having been used as the immunogens. Thus, hybridomas producing anti-HB-EGF antibodies were obtained.

Example 2

<Reactivities of Obtained Antibodies with Cell Surface HB-EGF>

Figure 1:
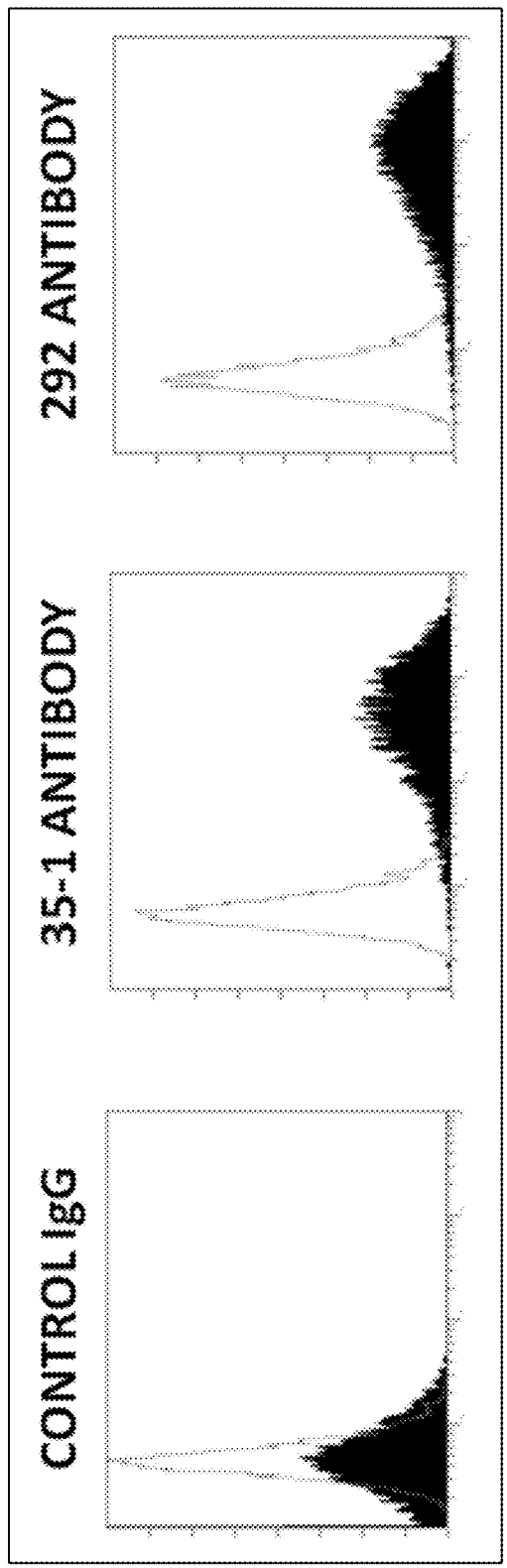
FIG. 1 shows histograms for illustrating the result of analyzing, by flow cytometry, the reactivities between obtained antibodies against a human HB-EGF protein (35-1 antibody and 292 antibody) and a cell line expressing a human HB-EGF protein on the cell surface (HB-EGF/st293T) or a cell line not expressing the protein on the cell surface (293T). In the figure, white histograms illustrate the reactivities between each antibody and the 293T (negative control), while black histograms illustrate the reactivities between each antibody and the HB-EGF/st293T. The vertical axis represents the cell count, while the horizontal axis represents the reactivity between the antibody and the cell line (mean fluorescence intensity).

Among the anti-HB-EGF antibodies obtained in Example 1, ones strongly reacted with cell surface HB-EGF were selected by a general method using flow cytometry. Each of the obtained antibodies at the same concentration (5 µg/mL) and a secondary antibody (manufactured by Beckman Coulter, Inc., catalog number: IM0855, this antibody was diluted to 1/200 for use) at the same concentration were allowed to react with the same number of HB-EGF/st293T (5×10^4) or 293T (5×10^4), and the mean fluorescence intensity was analyzed by the flow cytometry. Note that, in this flow cytometry, mouse IgG1 (isotype control, manufactured by MBL Co., Ltd., catalog number: M075-3) was used as a control antibody as a negative control, and confirmed not to react with the HB-EGF/st293T or 293T. FIG. 1 shows the obtained result.

As shown in FIG. 1, it was revealed that the obtained antibodies such as a 35-1 antibody and a 292 antibody were antibodies strongly reacting with HB-EGF on the cell surface.

Example 3

<Epitope Analysis for Obtained Antibodies>

An attempt was made to identify epitopes to which the obtained antibodies bound, by analyzing the reactivities of the anti-HB-EGF antibodies with amino acid point mutant HB-EGF by the following method using the flow cytometry.

First, prepared were cells expressing amino acid point mutant HB-EGF to be subjected to the flow cytometry. To be more specific, genes encoding mutant HB-EGF shown in Table 1 were prepared by site-directed mutagenesis using the HB-EGF-pQCxmhIPG as a template. The obtained mutant HB-EGF genes were each inserted into an animal cell expression vector pQCxmhIPG to prepare a vector encoding each mutant HB-EGF. Then, the genes were introduced into 293T cells using these vectors and transiently expressed. Thus, cells expressing amino acid point mutant HB-EGF were prepared.

TABLE 1

| Mutant HB-EGF | Amino acid point mutation |
|---|---|
| D114A | alanine was substituted for aspartic acid at position 114 from the N-terminus of wild type HB-EGF |
| F115A | alanine was substituted for phenylalanine at position 115 from the N-terminus of wild type HB-EGF |
| I117A | alanine was substituted for isoleucine at position 117 from the N-terminus of wild type HB-EGF |
| S131A | alanine was substituted for serine at position 131 from the N-terminus of wild type HB-EGF |
| G137A | alanine was substituted for glycine at position 137 from the N-terminus of wild type HB-EGF |
| Y138A | alanine was substituted for tyrosine at position 138 from the N-terminus of wild type HB-EGF |
| H139A | alanine was substituted for histidine at position 139 from the N-terminus of wild type HB-EGF |
| G140A | alanine was substituted for glycine at position 140 from the N-terminus of wild type HB-EGF |
| E141H | histidine was substituted for glutamic acid at position 141 from the N-terminus of wild type HB-EGF |
| R142A | alanine was substituted for arginine at position 142 from the N-terminus of wild type HB-EGF |
| H144A | alanine was substituted for histidine at position 144 from the N-terminus of wild type HB-EGF |
| G145A | alanine was substituted for glycine at position 145 from the N-terminus of wild type HB-EGF |

Moreover, to prepare a positive control in the flow cytometry, the gene was introduced into 293T cells using the HB-EGF-pQCxmhIPG and transiently expressed. Thus, cells expressing wild type HB-EGF were prepared.

Figure 2:
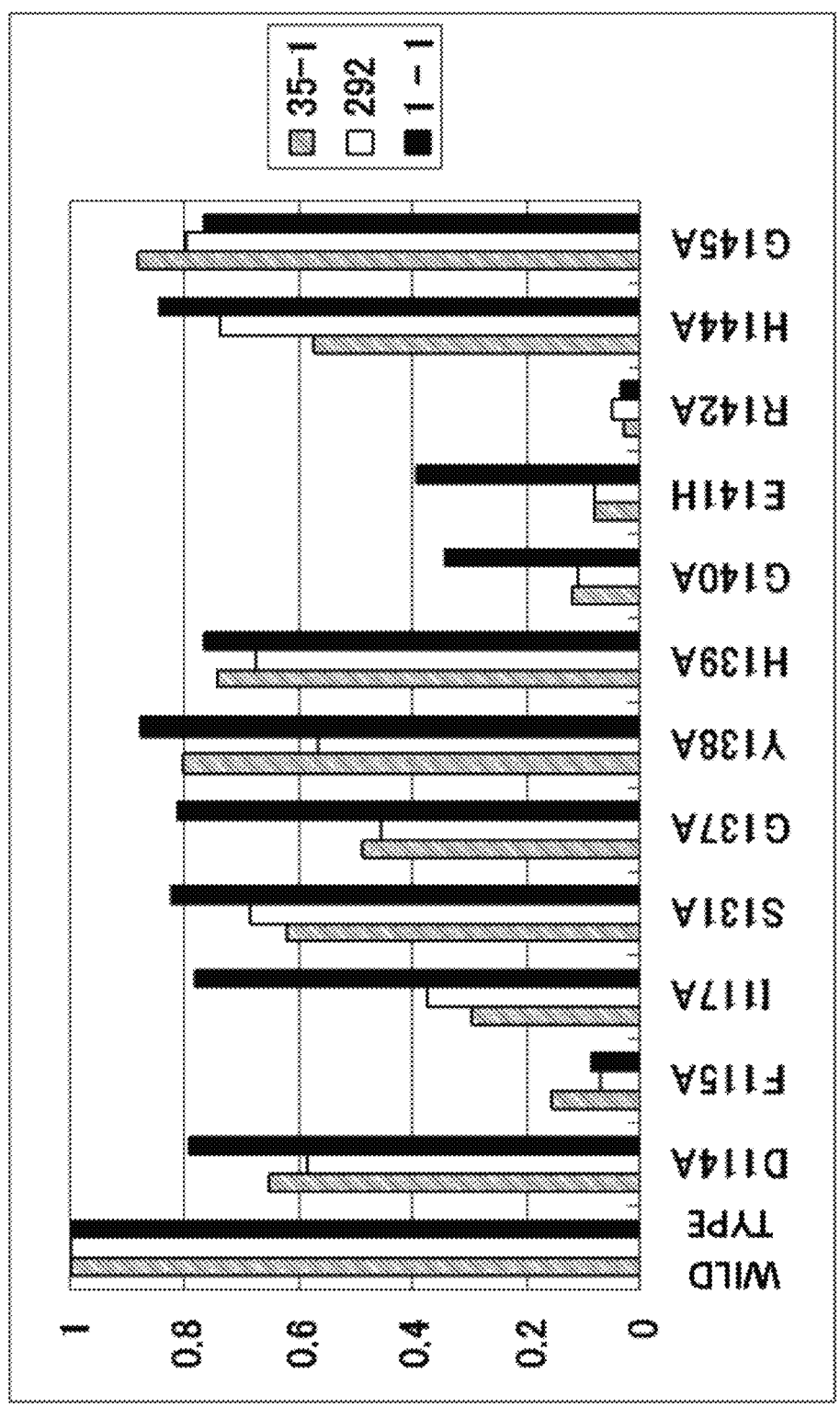
FIG. 2 is a graph for illustrating the result of analyzing, by flow cytometry, the reactivities between the antibodies against a human HB-EGF protein (the 35-1 antibody, the 292 antibody, and a 1-1 antibody) and each amino ac id mutant of the human HB-EGF protein. The vertical axis represents the binding strength (relative value) of each antibody to each amino acid mutant.

Next, each of the anti-HB-EGF antibodies (5 μg/mL) and a secondary antibody (manufactured by Beckman Coulter, Inc., catalog number: IM0855, this antibody was diluted to 1/200 for use)) were allowed to react with the cells expressing the wild type HB-EGF or each mutant HB-EGF, and the mean fluorescence intensity was analyzed by the flow cytometry. Further, to correct a difference in the amounts of the mutants expressed, a goat-derived anti-human HB-EGF polyclonal antibody (manufactured by R&D Systems, Inc., catalog number: BAF259, this antibody was used at a concentration of 1 μg/ml) whose binding ability did not change even if an amino acid point mutation occurred was allowed to react with SA-PE (manufactured by Invitrogen Corporation, catalog number: S866, this antibody was diluted to 1/200 for use), and the mean fluorescence intensity was analyzed by the flow cytometry as in the case of the anti-HB-EGF antibodies. Then, based on the obtained mean fluorescence intensity (antibody reactivity), the binding strength (relative value) of each anti-HB-EGF antibody to each mutant HB-EGF was calculated according to the following formula (Formula *). FIG. 2 shows the obtained result.

(the reactivity of an anti-HB-EGF antibody with mutant HB-EGF/the reactivity of the goat polyclonal antibody with the mutant HB-EGF)/(the reactivity of the anti-HB-EGF antibody with the wild type HB-EGF/the reactivity of the goat polyclonal antibody with the wild type HB-EGF). Formula*

Additionally, if the above-described binding strength (relative value) of an anti-HB-EGF antibody to mutant HB-EGF is 0.4 or less, it was determine that the anti-HB-EGF antibody was an antibody capable of binding to an amino acid before the substitution of the mutant.

As apparent from the result shown in FIG. 2, the 35-1 antibody and the 292 antibody hardly reacted with G140A, E141H, and R142A, and also the reactivities with F115A and I117A were significantly low. Moreover, a 1-1 antibody, one of the antibodies obtained this time, hardly reacted with F115A and R142A, and also the reactivities with G140A and E141H were significantly low.

Thus, it was revealed that among the obtained anti-HB-EGF antibodies, the 35-1 antibody and the 292 antibody recognized phenylalanine at position 115, isoleucine at position 117, glycine at position 140, glutamic acid at position 141, and arginine at position 142 of the human HB-EGF protein. Moreover, it was revealed that the 1-1 antibody recognized phenylalanine at position 115, glycine at position 140, glutamic acid at position 141, and arginine at position 142, but did not recognized isoleucine at position 117 unlike the two antibodies.

Example 4

<HB-EGF Cleavage Inhibitory Activities of Obtained Antibodies>

Whether or not the obtained anti-HB-EGF antibodies were capable of inhibit ing cleavage of transmembrane HB-EGF was evaluated by the following flow cytometry.

First, the HA-HB-EGF/stCHO-K1 was seeded into a 48-well microplate in an amount of 100000 cells per well, and cultured at 37° C. for 6 hours. After it was confirmed that the cells adhered to the bottom surface of the plate, the medium was replaced with an F12 Ham's medium containing no serum, and the resultant was further cultured for 15 hours.

Next, the medium was replaced with a medium to which the 35-1 antibody or a control antibody (manufactured by MBL Co., Ltd., catalog number: M075-3) had been added, and incubated at 37° C. for 30 minutes. In this event, the antibody concentration was set to five levels of 25, 5, 1, 0.2, and 0.04 μg/mL, and the amount of the medium per well was 200 μL. Subsequently, a medium supplemented with PMA having been adjusted to 5000 nM was added in an amount of 2 μL per well and mixed together, so that PMA was added at a final concentration of 500 nM. After cultured at 37° C. for 60 minutes, the cells were exfoliated with PBS-0.05% EDTA and collected. Note that it has been revealed that PMA (phorbol-12-myristate-13-acetate) added to the medium activates protein kinase C (PKC), thereby inducing HB-EGF shedding.

Figure 3:
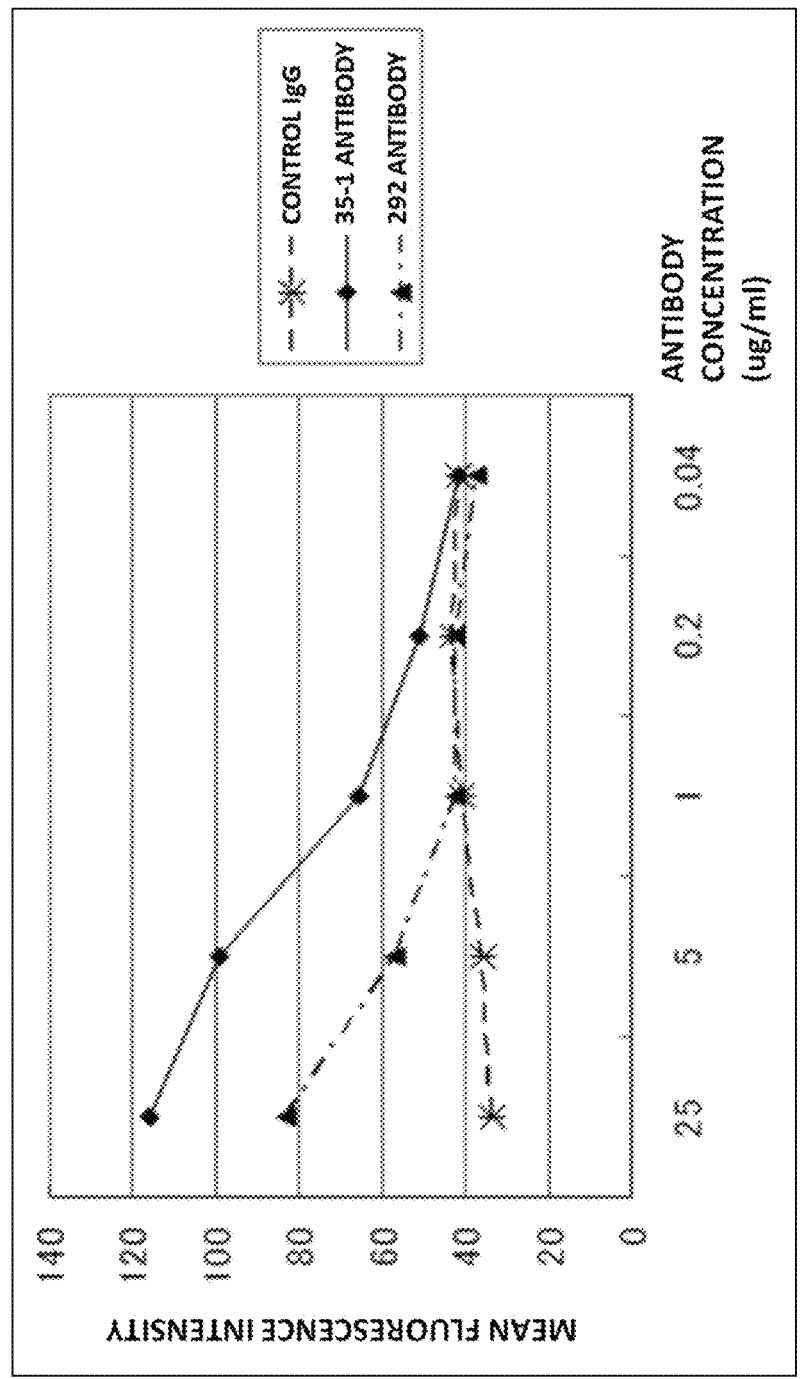
FIG. 3 is a graph for illustrating the result of analyzing the antibodies of the present invention (the 35-1 antibody and the 292 antibody) by flow cytometry for the activity of suppressing the human HB-EGF protein cleavage that would occur by PMA. The vertical axis represents the amount of the human HB-EGF protein (mean fluorescence intensity) remaining on the surface of cells (HA-HB-EGF/stCHO-K1) after PMA was added. The horizontal axis represents the concentration of each antibody added to the cells.

After the series of treatments, HB-EGF remaining on the surfaces of these cells was detected and analyzed by the flow cytometry using an antibody capable of recognizing the HA tag added to the N-terminus of the HB-EGF. The analysis was performed according to a conventional method using a biotinylated anti-HA tag antibody (manufactured by MBL Co., Ltd., catalog number: M132-3) having been diluted to 2 μg/mL as a primary antibody, and PE-labeled streptavidin (manufactured by Invitrogen Corporation, catalog number: 5866) having been diluted to 1/100 as a secondary antibody. FIG. 3 shows the obtained result. Note that, in FIG. 3, the vertical axis represents the mean fluorescence intensity in the flow cytometry.

As apparent from the result shown in FIG. 3, both of the 35-1 antibody and the 292 antibody increased the amount of the HB-EGF remaining on the cell surface in a manner dependent on the concentration of the antibodies added.

Next, whether or not the obtained anti-HB-EGF antibodies were capable of inhibiting the cleavage of transmembrane HB-EGF was evaluated by the following western blot.

First, the HA-HB-EGF/stCHO-K1 was seeded into a 48-well microplate in an amount of 100000 cells per well, and cultured at 37° C. for 6 hours. After it was confirmed that the cells adhered to the bottom surface of the plate, the medium was replaced with an F12 Ham's medium containing no serum, and the resultant was further cultured for 15 hours.

Then, the medium was replaced with a medium to which the 35-1 antibody or a control antibody (manufactured by MBL Co., Ltd., catalog number: M075-3) had been added, and incubated at 37° C. for 30 minutes. In this event, the antibody concentration was set to levels of 100, 10, and 1 μg/mL, and the amount of the medium per well was 200 μL.

Subsequently, a medium supplemented with PMA having been adjusted to 5000 nM was added in an amount of 2 μL per well and mixed together, so that PMA was added at a final concentration of 500 nM. Moreover, to measure the amount of HB-EGF-CTF under a condition where the cleavage by PMA was not induced, cells were prepared to which only a medium was added. Further, to measure the amount of HB-EGF-CTF formed in the non-inhibiting event, cells were prepared to which no antibody was added but only PMA was added. After these cells were cultured at 37° C. for 60 minutes, the cells were collected using an SDS sample buffer (62.5 mM Tris-HCL (pH=6.8), 5% glycerol, 2% SDS, 0.003% BPB, 5% 2-mercaptoethanol) in an amount of 100 μL per well.

Figure 4:
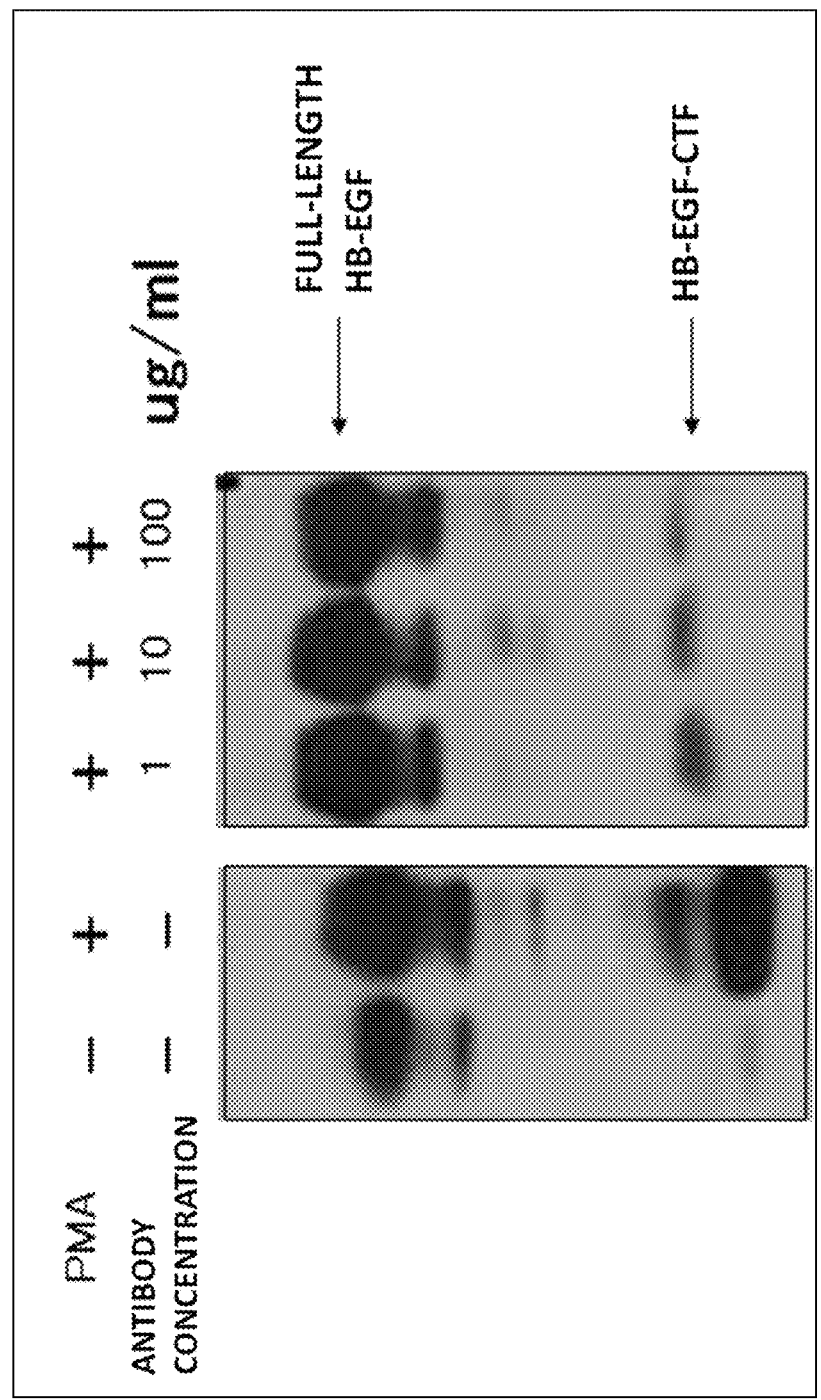
FIG. 4 shows photographs for illustrating the result of analyzing the antibody of the present invention (35-1 antibody) by western blot for the activity of suppressing the human HB-EGF protein cleavage that would occur by PMA. Note that, in the figure, "HB-EGF-CTF" indicates a partial protein (HB-EGF C-terminal fragment) formed and remaining at the cell membrane side after the human HB-EGF protein (the full-length HB-EGF) was cleaved (the same shall apply to FIG. 5).

After the series of treatments, HB-EGF-CTF in these cells was detected and analyzed by the western blot using an antibody capable of recognizing a myc tag added to the C-terminus of HB-EGF. The collected cell sample was heat treated and then subjected to SDS-PAGE in an amount of 10 μL at a time, and the analysis was performed according to a conventional method using an anti-myc tag antibody (manufactured by MBL Co., Ltd., catalog number: M047-3) having been diluted 5000 times as a primary antibody, and an HRP-labeled anti-mouse IgG antibody (manufactured by MBL Co., Ltd., catalog number: 330) having been diluted 5000 times as a secondary antibody. FIG. 4 shows the obtained result.

Figure 5:
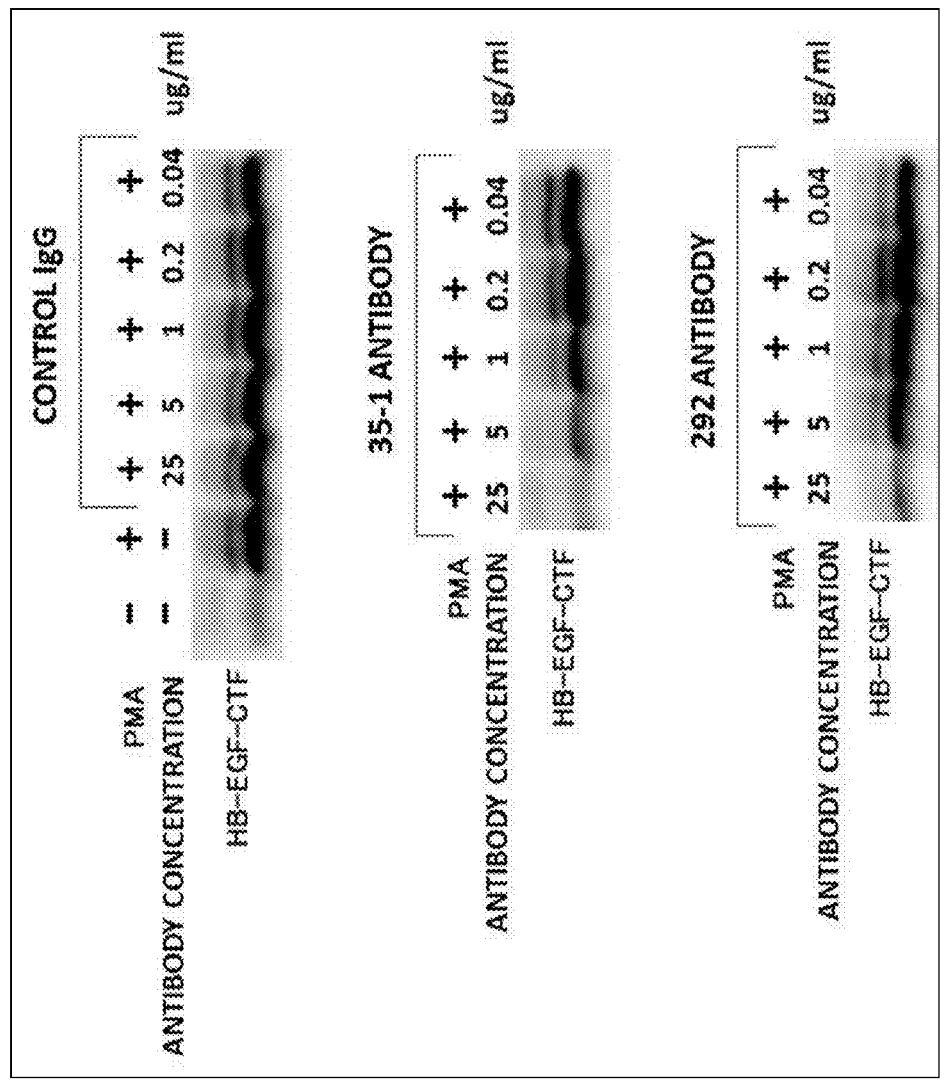
FIG. 5 shows photographs for illustrating the result of analyzing the antibodies of the present invention (the 35-1 antibody and the 292 antibody) by western blot for the activity of suppressing the human HB-EGF protein cleavage that would occur by PMA.

Furthermore, the incubation conditions were changed such that the HA-HB-EGF/stCHO-K1 was incubated together with the 35-1 antibody, the 292 antibody, or the control antibody which were added to the medium at a concentration of 25, 5, 1, 0.2, or 0.04 μg/mL. Whether or not these antibodies were capable of inhibiting the cleavage of transmembrane HB-EGF was evaluated by the western blot as described above. FIG. 5 shows the obtained result.

As apparent from the results shown in FIGS. 4 and 5, in both the cases of the 35-1 antibody and the 292 antibody, adding the antibody reduced the amount of the HB-EGF-CTF formed and remaining at the cell membrane side after the cleavage. Moreover, although unillustrated, the 1-1 antibody also reduced the amount of the HB-EGF-CTF formed and remaining at the cell membrane side after the cleavage like the two antibodies.

The above results revealed that the 35-1 antibody, the 292 antibody, and the 1-1 antibody exhibited an activity of inhibiting the cleavage of transmembrane HB-EGF.

Example 5

<HB-EGF Neutralizing Activities of Obtained Antibodies>

Whether the obtained anti-HB-EGF antibodies were capable of inhibiting EGFR phosphorylation induced when stimulated with HB-EGF, in other words, whether or not the anti-HB-EGF antibodies had an activity of neutralizing HB-EGF, was analyzed by the following western blot method using a human lung cancer culture cell line A431 (ATCC, catalog number: CRL-1555).

First, A431 having been cultured using DMEM-10% FBS (containing Penicillin-Streptomycin) was seeded into a 12-well plate in an amount of 50000 cells per well, and cultured at 37° C. for 6 hours. After it was confirmed that the cells adhered to the bottom surface of the plate, the medium was replaced with a DMEM medium containing no serum, and the resultant was further cultured for 48 hours.

Next, a soluble HB-EGF recombinant protein (HB-EGFv5) and the obtained anti-HB-EGF antibody (the 35-1 antibody, the 292 antibody, or the 1-1 antibody) were mixed in 200 μL of a DMEM medium containing no serum, and incubated at 37° C. for 30 minutes. Then, the above-described cells were added thereto. In this event, the recombinant protein concentration was 50 ng/mL, and the antibody concentration was set to six levels of 125, 25, 5, 1, 0.2, and 0 μg/mL. Additionally, the 35-1 antibody was tested also at low concentration (six levels of 10, 1, 0.1, 0.01, 0.001, and μg/mL). Moreover, the HB-EGF recombinant protein (HB-EGFv5) was solely added as a positive control, while a DMEM medium containing no HB-EGF was solely added as a negative control. After these were cultured at 37° C. for 15 minutes, the cells were collected using an SDS sample buffer (62.5 mM Tris-HCL (pH=6.8), 5% glycerol, 2% SDS, 0.003% BPB, 5% 2-mercaptoethanol) in an amount of 150 μL of per well.

Figure 6:
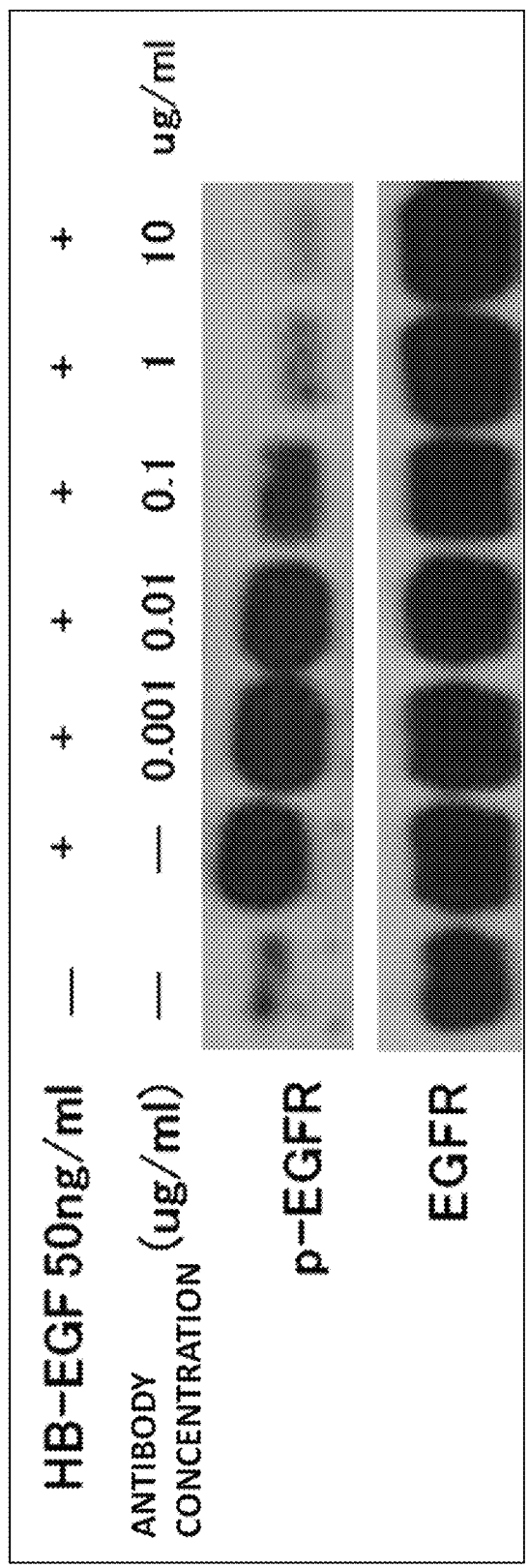
FIG. 6 shows photographs for illustrating the result of analyzing the antibody of the present invention (35-1 antibody) by western blot for the activity of suppressing the EGFR phosphorylation that would be induced by the human HB-EGF protein. In the figure, "EGFR" shows the amount of the EGFR protein in each cell, and "p-EGFR" shows the amount of the EGFR protein phosphorylated in each cell (regarding the representation in the figure, the same shall apply to FIGS. 7 and 8).
Figure 7:
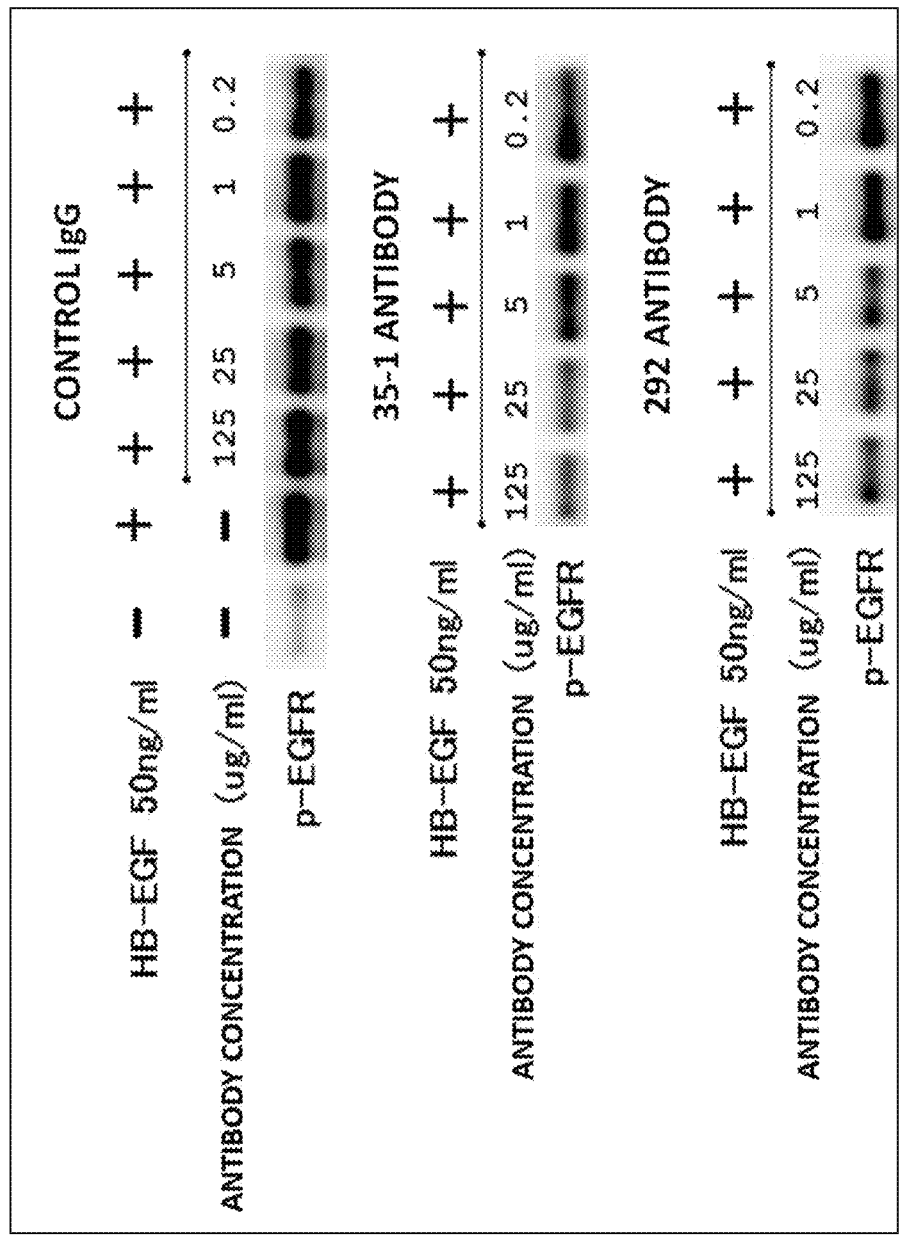

Further, the collected cell sample was heat treated and then subjected to SDS-PAGE in an amount of 15 μL at a time, followed by the western blot using an anti-phosphorylation EGFR rabbit antibody (manufactured by Cell Signaling Technology, Inc., catalog number: #3777) having been diluted to 1/1000 or an EGFR rabbit antibody (manufactured by Cell Signaling Technology, Inc., catalog number: #4267) and an HRP-labeled anti-rabbit antibody (manufactured by MBL Co., Ltd., catalog number: 458) having been diluted to 1/5000. FIGS. 6 to 8 show the obtained result.

As apparent from the result shown in FIGS. 6 and 7, both of the 35-1 antibody and the 292 antibody inhibited the EGFR phosphorylation attributable to HB-EGF in a concentration dependent manner. It was revealed that both the 35-1 antibody and the 292 antibody had an HB-EGF neutralizing activity. On the other hand, as apparent from the result shown in FIG. 8, the 1-1 antibody was not observed to inhibit the EGFR phosphorylation attributable to HB-EGF. It was revealed that the 1-1 antibody did not have an HB-EGF neutralizing activity.

As described above, the 35-1 antibody and the 292 antibody are different from the 1-1 antibody in whether isoleucine at position 117 of the human HB-EGF protein is included as the epitope or not. Moreover, NPL 21 has shown that both of antibodies (7E10, 3D9) whose epitope is isoleucine at position 133 and histidine at position 135 of a human HB-EGF protein and antibodies (3H4 and the like) whose epitope is glutamic acid at position 141 have a cleavage inhibitory activity but do not have a neutralizing activity.

Thus, it was revealed that in order for an anti-HB-EGF antibody to exhibit a neutralizing activity, it was necessary to bind to isoleucine at position 117 of the human HB-EGF protein.

Example 6

<Anti-Tumor Activity Evaluation Using Advanced Cancer Model>

To determine the anti-tumor activity of the obtained anti-HB-EGF antibody, the evaluation was performed using xenograft mice. To be more specific, first, a human breast cancer cell line MDA-MB-231 (ATCC, catalog number: HTB-26) was cultured using DMEM-10% FBS (containing Penicillin-Streptomycin), and exfoliated with PBS-0.05% EDTA. After washed with PBS, the resultant was suspended in an RPMI 1640 medium to be $5 \times 10^7$ cells/mL. An equal amount of Matrigel (manufactured by BD, catalog number: 354230) was added thereto, and the mixture was suspended. Then, 200 μL of the suspension was subcutaneously transplanted into the right ventral part of each 6-week old female nude mouse (manufactured by CLEA Japan, Inc., BALB/cAJcl-nu/nu). Mice were selected such that when a tumor volume reached approximately 200 mm$^3$, each group would have an average tumor volume equivalent to this volume. On the same day, 200 μL of an antibody solution having been diluted with PBS to 750 μg/ml (high concentration) or 150 μg/ml (low concentration) was intraperitoneally administered, whereas 200 μL of PBS was intraperitoneally administered in a control group (four mice in each group). Note that the antibody administered to the xenograft mice was a chimerized 35-1 antibody to be described later. In addition, the administration was carried out twice a week, six times in total. When and after the antibody was administered, the tumor diameter was measured with a vernier caliper. The tumor volume was calculated according to the following equation.

tumor volume (mm$^3$)=major axis×minor axis$^2$×0.5         Equation

FIG. 9 shows the obtained result.

As apparent from the result shown in FIG. 9, the 35-1 antibody inhibited the proliferation of the human breast cancer cell line MDA-MB-231. In other words, it was revealed that the 35-1 antibody had an anti-tumor activity against the advanced cancer model.

Example 7

<Evaluation of Antibody-Dependent Cell-Mediated Cytotoxicity Activity (ADCC Activity)>

The ADCC activity of the obtained anti-HB-EGF antibody was evaluated. To be more specific, first, the human breast cancer cell line MDA-MB-231 was selected as target cells. Then, the cells was cultured using DMEM-10% FBS (containing Penicillin-Streptomycin), and exfoliated with PBS-0.05% EDTA. After washed with PBS, the resultant was prepared to the optimal concentration using DMEM-10% FBS (containing Penicillin-Streptomycin). Peripheral blood mononuclear cells (PBMC) were prepared as effector cells from peripheral blood derived from a healthy person by the following method. The healthy person-derived peripheral blood was collected using a VENOJECT II vacuum blood-collecting tube (TERUMO CORPORATION), and diluted by adding the same amount of a saline thereto. The diluted peripheral blood was overlaid on Histopaque-1077 (manufactured by sigma-aldrich co., catalog number: 10771-500ML), and centrifuged at 800 g for 20 minutes to collect the peripheral blood mononuclear cells. Then, the peripheral blood mononuclear cells were washed with PBS and subsequently prepared to the optimal concentration using DMEM-10% FBS (containing Penicillin-Streptomycin).

The ADCC activity was evaluated as follows. Concretely, 25 μL of the effector cells and 50 μL of the target cells were dispensed in a 96-well U-bottom plate (manufactured by Sumitomo Bakelite Co., Ltd., catalog number: MS-309UR) such that the ratio of the target cells to the effector cells was 1:20. Then, to the resultant, 25 μL of the antibody having been diluted with DMEM-10% FBS (containing Penicillin-Streptomycin) to each concentration was added and incubated in 5% $CO_2$ at 37° C. for 20 hours. Note that the antibody added to the cells was the chimerized 35-1 antibody to be described later.

After the incubation with the antibody, the resultant was centrifuged at 200 g for 1 minute, and 50 μL of the supernatant was collected into a 96-well plate. Subsequently, the lactate dehydrogenase (LDH) activity in the supernatant was measured using CYTOTOX 96 Non-Radioactive Cytotoxicity Assay (manufactured by Promega Corporation, code number: G1780). Moreover, an LDH value of the effector cells, an LDH value of the target cells, and also an LDH value at the maximum cytotoxicity of the target cells solubilized using a lysis solution (9% TritonX-100) attached to CYTOTOX 96 Non-Radioactive Cytotoxicity Assay were measured as in the case of the LDH value in the experimental section to which the effector cells, the target cells, and the antibody were added. The ADCC activity was determined according to the following equation.

cytotoxic activity %=(the LDH value in the experimental section−the LDH value of the effector cells−the LDH value of the target cells)/(the LDH value at the maximum cytotoxicity−the LDH value of the target cells)×100%         Equation FIG. 10 shows the obtained result.

As apparent from the result shown in FIG. 10, the 35-1 antibody exhibited a cytotoxic activity in an antibody-concentration dependent manner. Thus, it was revealed that the 35-1 antibody exhibited not only a neutralizing activity but also an ADCC anti-tumor effect on the cancer expressing HB-EGF.

Example 8

<Isolation of Heavy Chain and Light Chain Variable Region Genes of 35-1 and 292 Antibodies, and Identification of CDRs>

Each hybridoma was cultured, and the total RNA was extracted by a general method. Next, the cDNA was obtained by a 5'RACE method using GeneRacer Kit (manufactured by Invitrogen Corporation, catalog number: L1502-01). Using this cDNA as a template, PCR was carried out (35 cycles each consisting of [94° C. for 30 seconds, 57° C. for 30 seconds, 72° C. for 50 seconds]) with Platinum Taq DNA Polymerase High Fidelity (manufactured by Invitrogen Corporation, catalog number: 11304-029) using GeneRacer 5' Primer (5'-CGACTGGAGCACGAGGACACTGA-3', SEQ ID NO: 20), CH1 (mouse IgG1 constant region 1), and 3' Primer (5'-AATTTTCTTGTCCACCTGG-3', SEQ ID NO: 21), so that the gene (cDNA) of the antibody heavy chain variable region was amplified. On the other hand, as to the antibody light chain also, PCR was carried out in the same manner using GeneRacer 5' Primer and Ck (κ constant region) and 3' Primer (5'-CTAACACTCATTCCTGTTGAAGCTCT-3', SEQ ID NO: 22), so that the gene (cDNA) was amplified. Each of the amplified gene fragments was cloned in a pT7Blue T-vector (manufactured by Novagen Inc., catalog number: 69820), and analyzed for the sequence using an automated sequencer (manufactured by Applied Biosystems Inc.). Then, based on the obtained base sequences, the amino acid sequences of the heavy chain and light chain variable regions and the sequence of CDRs of each of the variable regions were determined. The results are as follows.

```
<Heavy chain variable region of 35-1 antibody>
                                    SEQ ID NO: 9
EVQLQQSGPELVKPRASVKISCKASGYSFSGYYMHWVKQSPEKSLEWIGE
INPSTGGITYNQKFKAKATLTVDRSSSTAYMQLKSLTSEDSAVYYCTRIT
WAFAYWGQGTLVTVSA <CDR1 of heavy chain variable region of 35-1
antibody>
                                    SEQ ID NO: 6
GYYMH <CDR2 of heavy chain variable region of 35-1
antibody>
                                    SEQ ID NO: 7
EINPSTGGITYNQKFKA SEQ ID NO: 8
<CDR3 of heavy chain variable region of 35-1
antibody>
ITWAFAY <Light chain variable region of 35-1 antibody>
                                    SEQ ID NO: 5
QIVLTQSPAIMSASPGEKVTMTCSASSSVTYMYWYQQKPGSSPRLLIYD
TSNLASGVPVRFSGSGSGTSYSLTISRMEAEDAATYYCQQWSSYPPTFG
GGTKLEIK <CDR1 of light chain variable region of 35-1
antibody>
                                    SEQ ID NO: 2
SASSSVTYMY <CDR2 of light chain variable region of 35-1
antibody>
                                    SEQ ID NO: 3
DTSNLAS <CDR3 of light chain variable region of 35-1
antibody>
                                    SEQ ID NO: 4
QQWSSYPPT <Heavy chain variable region of 292 antibody>
                                    SEQ ID NO: 17
EVQLQQSGPELVKPGASVKISCKASGYSFTGYYMHWVKQSPEKSLEWIGE
INPSTGGTTYNQKFKAKATLTLDKSSSTAYMQLKSLTSEDSAVYYCAKSP
YWDGAYWGQGTLVTVSA <CDR1 of heavy chain variable region of 292
antibody>
                                    SEQ ID NO: 14
GYYMH <CDR2 of heavy chain variable region of 292
antibody>
                                    SEQ ID NO: 15
EINPSTGGTTYNQKFKA <CDR3 of heavy chain variable region of 292
antibody>
                                    SEQ ID NO: 16
SPYWDGAY <Light chain variable region of 292 antibody>
                                    SEQ ID NO: 13
QIVLTQSPAIMSASPGEKVTMTCSASSSISYMYWYQQRPGSSPRLLIYDT
SNLASGVPVRFSGSGSGTSHSLTISRMEAEDAATYYCQQWSSYPSTFGGG
TKLEIK <CDR1 of light chain variable region of 292
antibody>
                                    SEQ ID NO: 10
SASSSISYMY <CDR2 of light chain variable region of 292
antibody>
                                    SEQ ID NO: 11
DTSNLAS <CDR3 of light chain variable region of 292
antibody>
                                    SEQ ID NO: 12
QQWSSYPST
```

Example 9

<Preparation of 35-1 Chimeric Antibody>

The following PCR amplification primers were designed based on the gene sequences thus determined, and the antibody variable regions were amplified by PCR. In this event, the secretion signal sequence was converted into a sequence recommended by Lonza Group, and restriction enzyme recognition sequences were added to ends of the amplified fragments (a HindIII recognition sequence and an XhoI recognition sequence were added for the heavy chain variable region, HindIII and BsiWI recognition sequences were added for the light chain variable region).

The obtained PCR products were cleaved with the above restriction enzymes, and inserted by a conventional method into human IgG1 antibody producing vectors of Lonza Group incorporating the human IgG1 constant region. These vectors were used to establish chimeric antibody-producing cell lines based on a protocol recommended by Lonza Group. From the culture supernatants, a chimeric antibody (35-1 chimeric antibody) was purified using Protein A.

Example 10

<Preparation of 35-1 Humanized Antibody>

A humanized antibody was prepared by a CDR-grafting method. Concretely, homology search was conducted on each of a framework region of the heavy chain variable region excluding the CDR sequences and a framework region of the light chain variable region excluding the CDR sequences to select a human antibody sequence of a heavy chain variable region having a homology of 73.5% with the 35-1 antibody and a human antibody sequence of a light chain variable region having a homology of 86.3% therewith. Using the human antibody sequences as template sequences, the CDR-grafting method was carry out to determine a variable region sequence having CDR sequences modified to those of 35-1. The synthesized variable region sequence was inserted by the conventional method into a human IgG1 antibody producing vector of Lonza Group incorporating the human IgG1 constant region. Thus, a 35-1 humanized antibody having a heavy chain variable region and a light chain variable region of the following sequences was prepared.

```
<Heavy chain variable region of 35-1 humanized
antibody>
                                      SEQ ID NO: 19
QVQLVQSGAEVVKPGSSVKVSCKASGYSFSGYYMHWVKQAPGQGLEWIG
EINPSTGGITYNQKFKAKATLTVDRSTSTAYMELKSLTSEDTAVYYCTR
ITWAFAYWGQGTTVTVSS <Light chain variable region of 35-1 humanized
antibody>
                                      SEQ ID NO: 18
QIVLTQSPTTMAASPGEKITITCSASSSVTYMYWYQQRPGFSPKLLIYD
TSNLASGVPVRFSGSGSGTSYSLTIGTMEAEDVATYYCQQWSSYPPTFG
GGTKLEIK
```

Example 11

<Reactivity of 35-1 Chimeric Antibody or 35-1 Humanized Antibody with Antigen>

The reactivity of the 35-1 chimeric antibody or the 35-1 humanized antibody with HB-EGF was evaluated by the flow cytometry.

The flow cytometry was performed by the above-described method using the culture supernatant of 293T cells in which a human IgG1 antibody producing vector expressing the 35-1 chimeric antibody or the 35-1 humanized antibody as a primary antibody had been introduced. The antibody concentration in the culture supernatant was calculated according to a sandwich ELISA method. In the sandwich ELISA method, a goat anti-mouse IgG (manufactured by MBL Co., Ltd., code number: 303G) was immobilized on a 96-well ELISA plate in an amount of 5 μg/mL, that is, 50 μL/well, and the culture supernatant of the 293T cells was allowed to react therewith in an amount of 50 μL/well for 1 hour. After the plate was washed with 0.05% Tween 20-PBS, an HRP-labeled goat anti-mouse IgG (manufactured by MBL Co., Ltd., code number: 330) having been diluted to 1/10000 was added as a detection antibody in an amount of 50 μL/well and left to stand at room temperature for 1 hour. After the plate was washed with 0.05% Tween 20-PBS, a color developing solution was added thereto in an amount of 50 μL/well and left to stand at room temperature for 20 minutes to develop a color. The color development was terminated by adding 1 M phosphoric acid in an amount of 50 μL/well. Then, the absorbance at 450 nm was measured with a plate reader. Regarding the antibody concentration in the culture supernatant, a standard curve was created based on measured values obtained by serially diluting the antibody solution of a known concentration, and the antibody concentration was calculated from the measured values of the culture supernatant. FIG. 11 shows the obtained result. As shown in FIG. 11, the 35-1 chimeric antibody and the 35-1 humanized antibody bound to HB-EGF in a concentration dependent manner. It was revealed that each maintained the reactivity with the antigen.

INDUSTRIAL APPLICABILITY

As has been described above, the present invention makes it possible to provide an antibody capable of binding to human HB-EGF, thereby inhibiting cleavage of the human HB-EGF and inhibiting binding between the human HB-EGF and an EGF receptor. Moreover, the antibody of the present invention is excellent also in the activity of suppressing tumor proliferation. Therefore, the antibody of the present invention is useful also in the treatment or prevention for cancers.

[Sequence Listing Free Text]
SEQ ID NO: 2
<223> CDR1 of Light Chain (35-1)
SEQ ID NO: 3
<223> CDR2 of Light Chain (35-1)
SEQ ID NO: 4
<223> CDR3 of Light Chain (35-1)
SEQ ID NO: 5
<223> Variable Region of Light Chain (35-1)
SEQ ID NO: 6
<223> CDR1 of Heavy Chain (35-1)
SEQ ID NO: 7
<223> CDR2 of Heavy Chain (35-1)
SEQ ID NO: 8
<223> CDR3 of Heavy Chain (35-1)
SEQ ID NO: 9
<223> Variable Region of Heavy Chain (35-1)
SEQ ID NO: 10
<223> CDR1 of Light Chain (292)
SEQ ID NO: 11
<223> CDR2 of Light Chain (292)
SEQ ID NO: 12
<223> CDR3 of Light Chain (292)
SEQ ID NO: 13
<223> Variable Region of Light Chain (292)
SEQ ID NO: 14
<223> CDR1 of Heavy Chain (292)
SEQ ID NO: 15
<223> CDR2 of Heavy Chain (292)
SEQ ID NO: 16
<223> CDR3 of Heavy Chain (292)
SEQ ID NO: 17
<223> Variable Region of Heavy Chain (292)
SEQ ID NO: 18
<223> Artificially Humanized Variable Region of Light Chain (35-1)
SEQ ID NO: 19
<223> Artificially Humanized Variable Region of Heavy Chain (35-1)
SEQ ID NOs: 20 to 22
<223> Artificially synthesized primer sequence

The invention claimed is:

1. An antibody capable of binding to human HB-EGF, wherein the antibody is an antibody which comprises a light chain variable region containing the amino acid sequences of SEQ ID NOs: 2 to 4, and wherein the antibody further comprises a heavy chain variable region containing the amino acid sequences of SEQ ID NOs: 6 to 8.

2. A composition comprising the antibody according to claim 1, and further comprising a pharmaceutically acceptable carrier or medium.

3. An antibody capable of binding to human HB-EGF, wherein the antibody is an antibody comprising a light chain variable region which comprises the amino acid sequence of SEQ ID NO: 5, or which comprises the amino acid sequence of SEQ ID NO: 5 but in which one to ten amino acids in the framework region are substituted, and
  wherein the antibody further comprises a heavy chain variable region which comprises the amino acid sequence of SEQ ID NO: 9, or which comprises the amino acid sequence of SEQ ID NO: 9 but in which one to ten amino acids in the framework region are substituted.

4. An antibody capable of binding to human HB-EGF, wherein the antibody comprises:
  a light chain variable region which comprises the amino acid sequence of SEQ ID NO: 18, or which comprises the amino acid sequence of SEQ ID NO: 18 but in which one to ten amino acids in the framework region are substituted; and
  a heavy chain variable region which comprises the amino acid sequence of SEQ ID NO: 19, or which comprises the amino acid sequence of SEQ ID NO: 19 but in which one to ten amino acids in the framework region are substituted.

* * * * *